US012661191B2

(12) United States Patent
Luo et al.

(10) Patent No.: US 12,661,191 B2
(45) Date of Patent: Jun. 23, 2026

(54) SYSTEM AND METHOD FOR RENDERING OPERATIVE GUIDANCE OVERLAY

(71) Applicant: IMMERSIVETOUCH, INC., Chicago, IL (US)

(72) Inventors: Jia Luo, Chicago, IL (US); Chris Orris, Chicago, IL (US); Pat Banerjee, Chicago, IL (US)

(73) Assignee: IMMERSIVETOUCH, INC., Chicago, IL (US)

( * ) Notice: Subject to any disclaimer, the term of this patent is extended or adjusted under 35 U.S.C. 154(b) by 0 days.

(21) Appl. No.: 19/395,111

(22) Filed: Nov. 20, 2025

(65) Prior Publication Data

US 2026/0076754 A1     Mar. 19, 2026

Related U.S. Application Data

(63) Continuation-in-part of application No. 18/990,047, filed on Dec. 20, 2024, which is a (Continued)

(51) Int. Cl.
 G06T 19/00         (2011.01)
 A61B 34/00         (2016.01)
         (Continued)

(52) U.S. Cl.
 CPC ............ *A61B 34/25* (2016.02); *A61B 90/361* (2016.02); *G06T 7/75* (2017.01); *G06T 19/006* (2013.01);
         (Continued)

(58) Field of Classification Search
 None
 See application file for complete search history.

(56) References Cited

U.S. PATENT DOCUMENTS

2018/0280090 A1   10/2018  Davies
2019/0080515 A1*   3/2019  Geri ........................ G06F 3/012
                        (Continued)

FOREIGN PATENT DOCUMENTS

AU       2022384283 A1    5/2024
WO       2023-086592 A3   5/2023

OTHER PUBLICATIONS

Extended European Search Report dated May 19, 2026 in EP 25222238.5.

*Primary Examiner* — Robert J Craddock
(74) *Attorney, Agent, or Firm* — DLA PIPER LLP US

(57)         ABSTRACT

Embodiments for rendering an operative guidance overlay in association with a patient are disclosed. A method includes receiving image data indicating an anatomical structure of the patient and a structure of operative instruments; generating virtual models based on the image data; receiving sensor data associated with a user, the operative instruments, or the patient; dynamically generating guidance overlay data associated with the anatomical structure of the patient, or the operative instruments based on the virtual models and the sensor data; and rendering the operative guidance overlay in association with the patient based on the guidance overlay data using a wearable augmented reality interface device. The virtual models include a virtual anatomical model of the anatomical structure of the patient, or virtual instrument models associated with the operative instruments. The rendering comprises continuous alignment of the virtual anatomical model with the patient and the virtual instrument models with the operative instruments.

20 Claims, 8 Drawing Sheets

1100

Related U.S. Application Data continuation-in-part of application No. 18/048,681, filed on Oct. 21, 2022, now Pat. No. 12,186,022, which is a continuation-in-part of application No. 17/859,655, filed on Jul. 7, 2022, now Pat. No. 12,213,750, which is a continuation-in-part of application No. 17/126,570, filed on Dec. 18, 2020, now Pat. No. 11,416,069, which is a continuation-in-part of application No. 16/839,803, filed on Apr. 3, 2020, now Pat. No. 10,872,460, which is a continuation-in-part of application No. 16/138,209, filed on Sep. 21, 2018, now Pat. No. 10,650,604.

(51) Int. Cl.
| | | |
|---|---|---|
| *A61B 90/00* | (2016.01) | |
| *G06T 7/73* | (2017.01) | |
| *G16H 40/67* | (2018.01) | |
| *A61B 34/10* | (2016.01) | |

(52) U.S. Cl.
CPC ........ *G16H 40/67* (2018.01); *A61B 2034/105* (2016.02); *A61B 2090/365* (2016.02); *A61B 2090/372* (2016.02); *G06T 2207/30004* (2013.01); *G06T 2207/30204* (2013.01); *G06T 2210/41* (2013.01)

(56) References Cited

U.S. PATENT DOCUMENTS

| | | | |
|---|---|---|---|
| 2019/0380785 A1 | 12/2019 | Davies | |
| 2020/0118339 A1* | 4/2020 | Sakai | G06T 19/20 |
| 2023/0015516 A1* | 1/2023 | Meglan | A61B 34/10 |
| 2024/0320935 A1 | 9/2024 | Pissarenko et al. | |

* cited by examiner

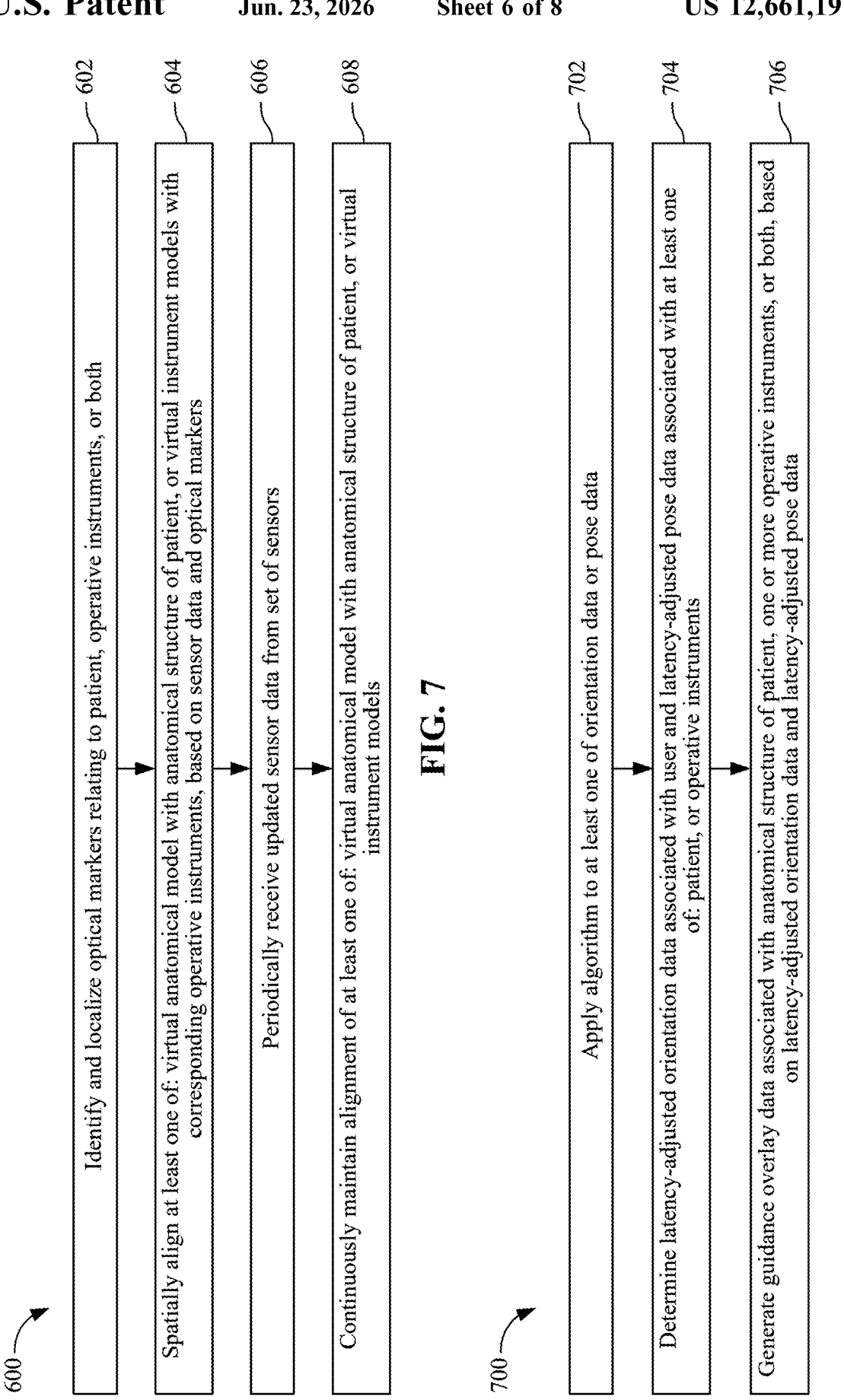

600

602 Identify and localize optical markers relating to patient, operative instruments, or both 604 Spatially align at least one of: virtual anatomical model with anatomical structure of patient, or virtual instrument models with corresponding operative instruments, based on sensor data and optical markers 606 Periodically receive updated sensor data from set of sensors 608 Continuously maintain alignment of at least one of: virtual anatomical model with anatomical structure of patient, or virtual instrument models

702 Apply algorithm to at least one of orientation data or pose data

704 Determine latency-adjusted orientation data associated with user and latency-adjusted pose data associated with at least one of: patient, or operative instruments 706 Generate guidance overlay data associated with anatomical structure of patient, one or more operative instruments, or both, based on latency-adjusted orientation data and latency-adjusted pose data

FIG. 8

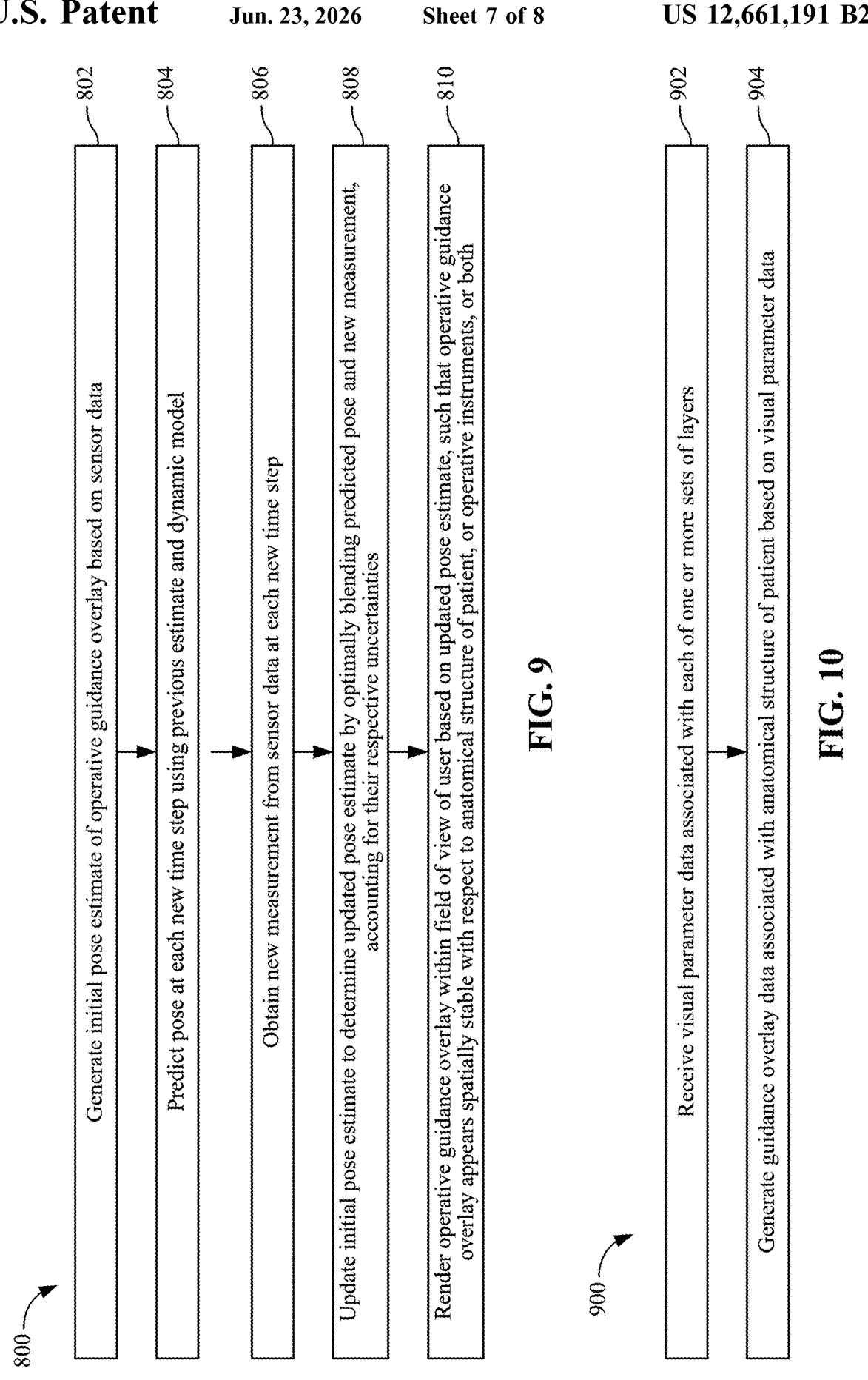

800

802 — Generate initial pose estimate of operative guidance overlay based on sensor data 804 — Predict pose at each new time step using previous estimate and dynamic model 806 — Obtain new measurement from sensor data at each new time step 808 — Update initial pose estimate to determine updated pose estimate by optimally blending predicted pose and new measurement, accounting for their respective uncertainties 810 — Render operative guidance overlay within field of view of user based on updated pose estimate, such that operative guidance overlay appears spatially stable with respect to anatomical structure of patient, or operative instruments, or both

902 — Receive visual parameter data associated with each of one or more sets of layers 904 — Generate guidance overlay data associated with anatomical structure of patient based on visual parameter data

FIG. 10

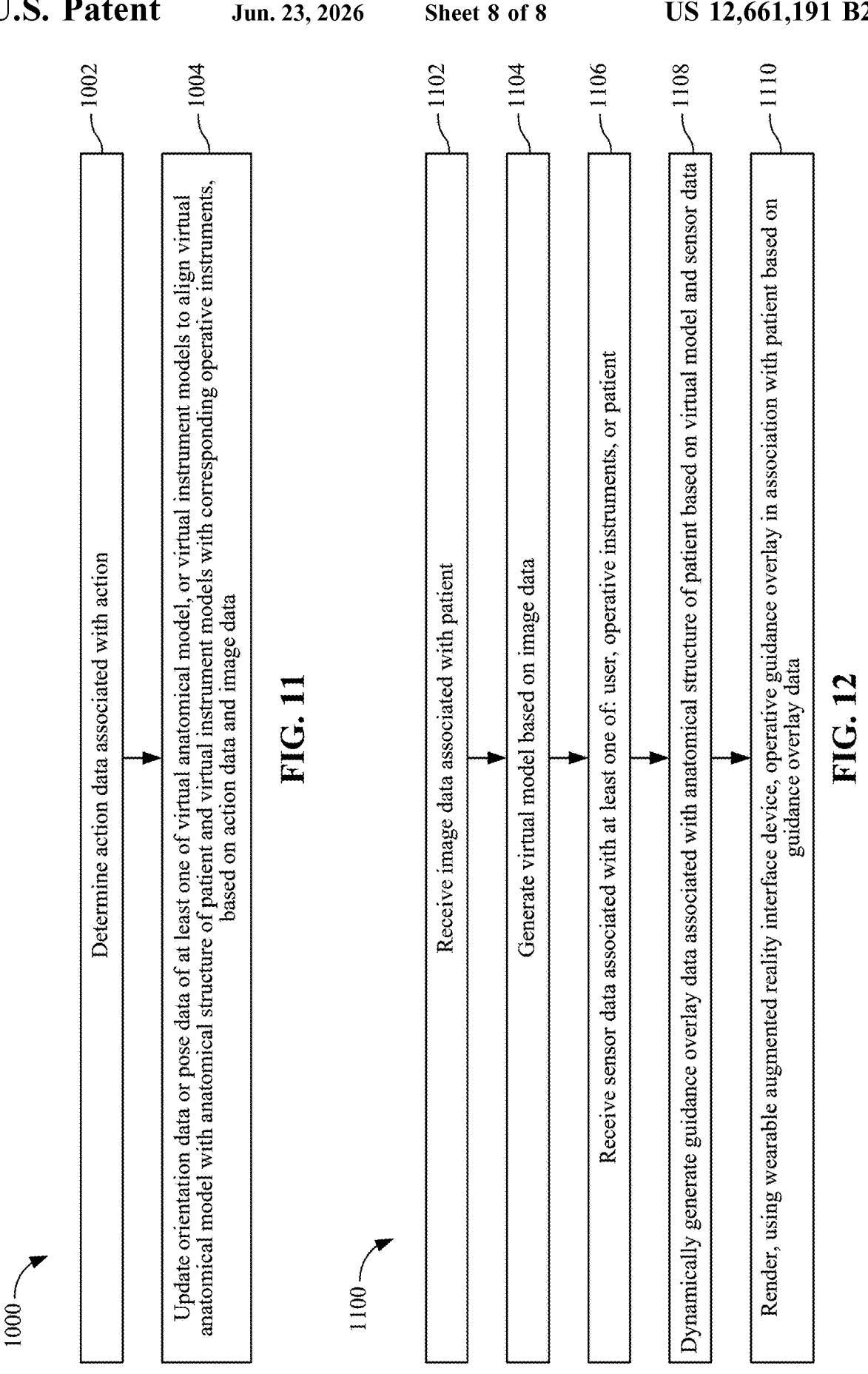

1000

1002 — Determine action data associated with action

1004 — Update orientation data or pose data of at least one of virtual anatomical model, or virtual instrument models to align virtual anatomical model with anatomical structure of patient and virtual instrument models with corresponding operative instruments, based on action data and image data

1102 — Receive image data associated with patient

1104 — Generate virtual model based on image data

1106 — Receive sensor data associated with at least one of: user, operative instruments, or patient 1108 — Dynamically generate guidance overlay data associated with anatomical structure of patient based on virtual model and sensor data 1110 — Render, using wearable augmented reality interface device, operative guidance overlay in association with patient based on guidance overlay data

FIG. 12

SYSTEM AND METHOD FOR RENDERING OPERATIVE GUIDANCE OVERLAY

CROSS-REFERENCE TO RELATED APPLICATIONS

This is a continuation in-part of U.S. application Ser. No. 18/990,047, filed Dec. 20, 2024, which is a continuation-in-part of U.S. application Ser. No. 18/048,681, filed Oct. 21, 2022, now U.S. Pat. No. 12,186,022, which is a continuation-in-part of U.S. application Ser. No. 17/859,655, filed Jul. 7, 2022, now U.S. Pat. No. 12,213,750, which is a continuation-in-part of U.S. application Ser. No. 17/126,570 filed Dec. 18, 2020, now U.S. Pat. No. 11,416,069, which is a continuation-in-part of U.S. application Ser. No. 16/839, 803 filed Apr. 3, 2020, now U.S. Pat. No. 10,872,460, which is a continuation-in-part of U.S. application Ser. No. 16/138, 209 filed Sep. 21, 2018, now U.S. Pat. No. 10,650,604. The above-mentioned applications and patents are incorporated herein by reference in their entirety.

TECHNICAL FIELD

The present application generally relates to systems and methods for visualizing, planning, or performing a medical procedure, and more particularly to systems and methods for rendering an operative guidance overlay in association with a virtual anatomical model of a patient and virtual instrument models with corresponding operative instruments.

BACKGROUND

The integration of immersive technologies such as augmented reality (AR), virtual reality (VR), and mixed reality (MR) is increasingly advancing the standards of surgical planning and intraoperative navigation in modern healthcare. These modalities enable enhanced visualization of patient-specific anatomy reconstructed from medical imaging data, providing spatial context and interaction that support more precise surgical decision-making. In particular, AR systems allow clinicians to visualize internal structures without invasive exposure. Such capabilities have demonstrated potential in fields like orthopedic, thoracic, and reconstructive surgery, where the complexity of anatomical variation demands tailored surgical strategies.

Despite the advancements in immersive visualization, surgical workflows largely continue to rely on traditional two-dimensional imaging or generic three-dimensional models that lack responsive alignment to the physical patient. These limitations often require surgeons to make approximations based on memory or indirect anatomical landmarks, increasing the risk of inaccurate incisions, tissue trauma, or suboptimal implant placement. The disconnect between preoperative planning and intraoperative execution can prolong procedures and increase the cognitive workload on the surgical team.

Moreover, conventional planning tools and intraoperative aids rarely incorporate detailed multi-layered anatomical information such as the relationship between bone, muscle, and soft tissue. This is especially problematic in surgeries involving trauma, fractures, or anatomical anomalies, where precise spatial understanding is critical. In such scenarios, the absence of integrated and accurate visualization tools may result in longer operative times, increased patient morbidity, and greater demand for intraoperative corrections or adjustments.

Therefore, there exists a need for an efficient and accurate approach to surgical planning and intraoperative guidance that enables precise anatomical localization, reduces operative complexity, and enhances surgical outcomes, thereby reducing procedural risks, shortening surgery durations, and improving overall clinical precision.

SUMMARY

One embodiment of the present application includes a system including a wearable augmented reality interface device, a set of sensors, and a computing device. The wearable augmented reality interface device is configured to present an operative guidance overlay within a field of view of a user. The set of sensors are arranged in association with the wearable augmented reality interface device. The set of sensors is configured to measure sensor data associated with at least one of: the user, one or more operative instruments, or a patient, and transmit the measured sensor data to one or more processors. The computing device comprises a memory configured to store computer-executable instructions and the one or more processors configured to execute the computer-executable instructions to receive image data associated with the patient. The image data indicates an anatomical structure of the patient and a structure of each of the one or more operative instruments. The one or more processors are configured to generate one or more virtual models based on the image data. The one or more virtual models comprise at least one of: a virtual anatomical model of the anatomical structure of the patient, or one or more virtual instrument models associated with the one or more operative instruments. The one or more processors are configured to receive the sensor data associated with at least one of: the user, the one or more operative instruments, or the patient. The one or more processors are configured to dynamically generate guidance overlay data associated with at least one of: the anatomical structure of the patient, or the one or more operative instruments, based on the one or more virtual models, and the sensor data. The guidance overlay data indicates the operative guidance overlay comprising one or more guidance markers associated with the patient, the one or more operative instruments, or both. The one or more processors are configured to render, using the wearable augmented reality interface device, the operative guidance overlay in association with the patient based on the guidance overlay data. The rendering comprises continuous alignment of the virtual anatomical model with the patient and the continuous alignment of the one or more virtual instrument models with corresponding operative instrument of the one or more operative instruments.

Another embodiment of the present application includes a method that includes receiving image data associated with a patient. The image data indicates an anatomical structure of the patient and a structure of each of one or more operative instruments. The method further includes generating one or more virtual models based on the image data. The one or more virtual models comprise at least one of: a virtual anatomical model of the anatomical structure of the patient, or one or more virtual instrument models associated with the one or more operative instruments. The method further includes receiving, from a set of sensors, sensor data associated with at least one of: a user, the one or more operative instruments, or the patient. The method further includes dynamically generating guidance overlay data associated with at least one of: the anatomical structure of the patient, or the one or more operative instruments, based on the one or more virtual models and the sensor data. The guidance overlay data indicates an operative guidance overlay comprising one or more guidance markers associated with the patient, the one or more operative instruments, or both. The method further includes rendering, using a wearable augmented reality interface device, the operative guidance overlay in association with the patient based on the guidance overlay data. The rendering comprises continuous alignment of the virtual anatomical model with the patient and the continuous alignment of the one or more virtual instrument models with a corresponding operative instrument of the one or more operative instruments.

In yet another embodiment of the present application includes a computer programmable product that includes a non-transitory computer-readable medium having stored thereon computer-executable instructions, which when executed by one or more processors, cause the one or more processors to carry out operations including receiving image data associated with a patient. The image data indicates an anatomical structure of the patient and a structure of each of one or more operative instruments. The operations further include generating one or more virtual models based on the image data. The one or more virtual models comprise at least one of: a virtual anatomical model of the anatomical structure of the patient, or one or more virtual instrument models associated with the one or more operative instruments. The operations further include receive, from a set of sensors, sensor data associated with at least one of: a user, the one or more operative instruments, or the patient. The operations further include dynamically generating guidance overlay data associated with at least one of: the anatomical structure of the patient, or the one or more operative instruments, based on the one or more virtual models and the sensor data. The guidance overlay data indicates an operative guidance overlay comprising one or more guidance markers associated with the patient, the one or more operative instruments, or both. The operations further include rendering, using a wearable augmented reality interface device, the operative guidance overlay in association with the patient based on the guidance overlay data. The rendering comprises continuous alignment of the virtual anatomical model with the patient and the continuous alignment of the one or more virtual instrument models with a corresponding operative instrument of the one or more operative instruments.

Other and further aspects and features of the present application would be evident from reading the following detailed description of the embodiments, which are intended to illustrate, not limit, the present application.

BRIEF DESCRIPTION OF THE DRAWINGS

Figure 1:
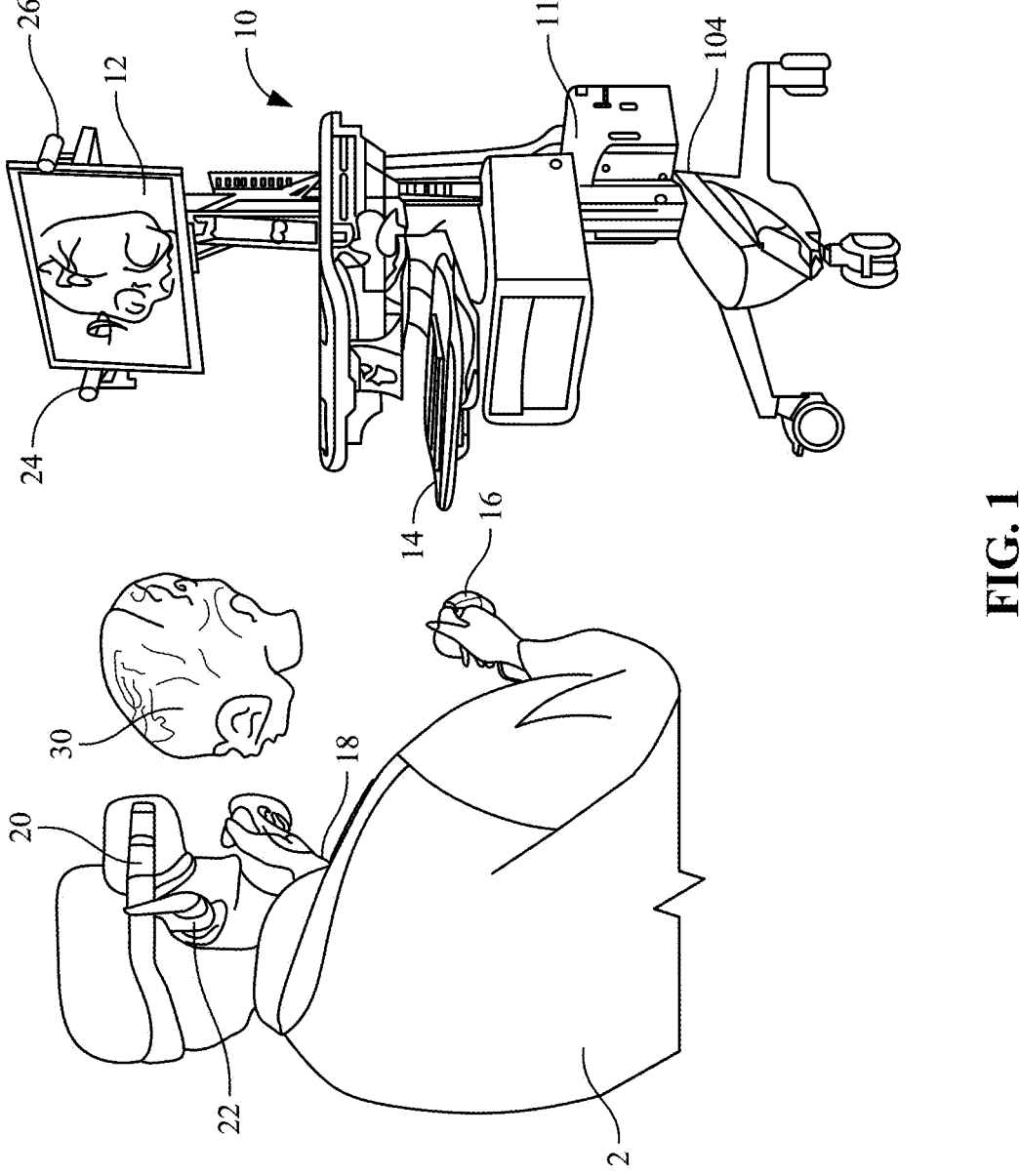
Figure 2:
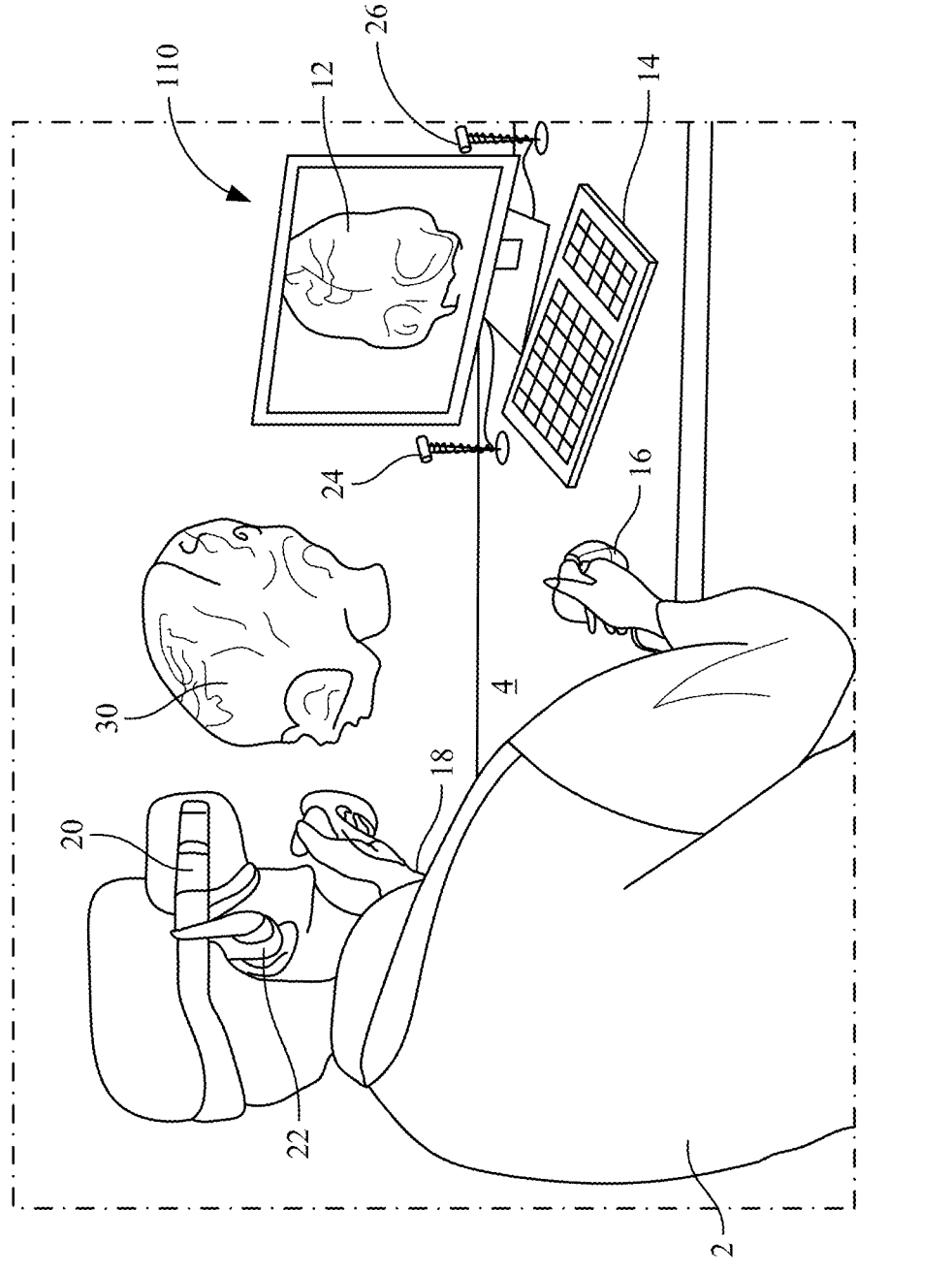
Figure 3:
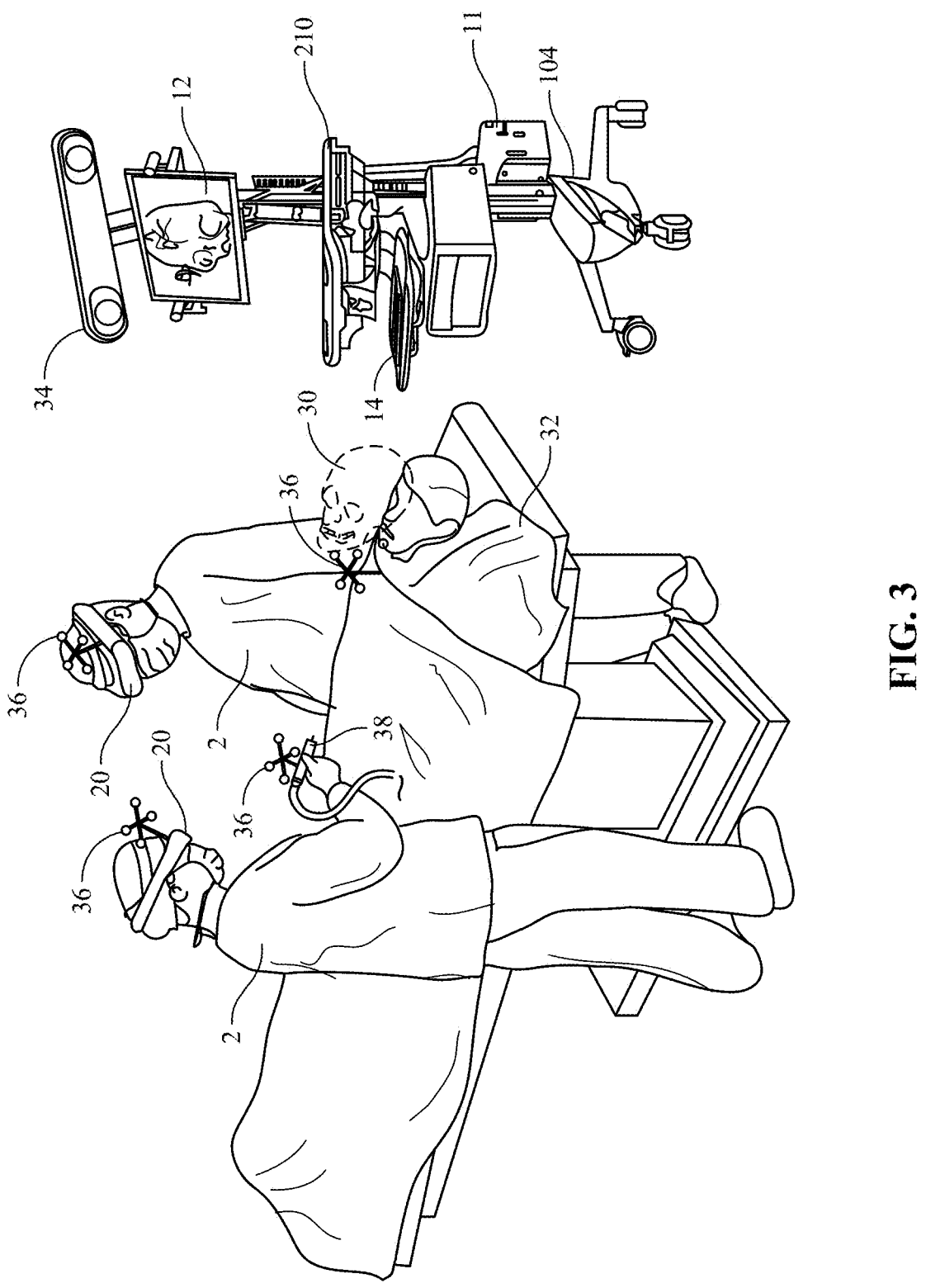
Figure 4:
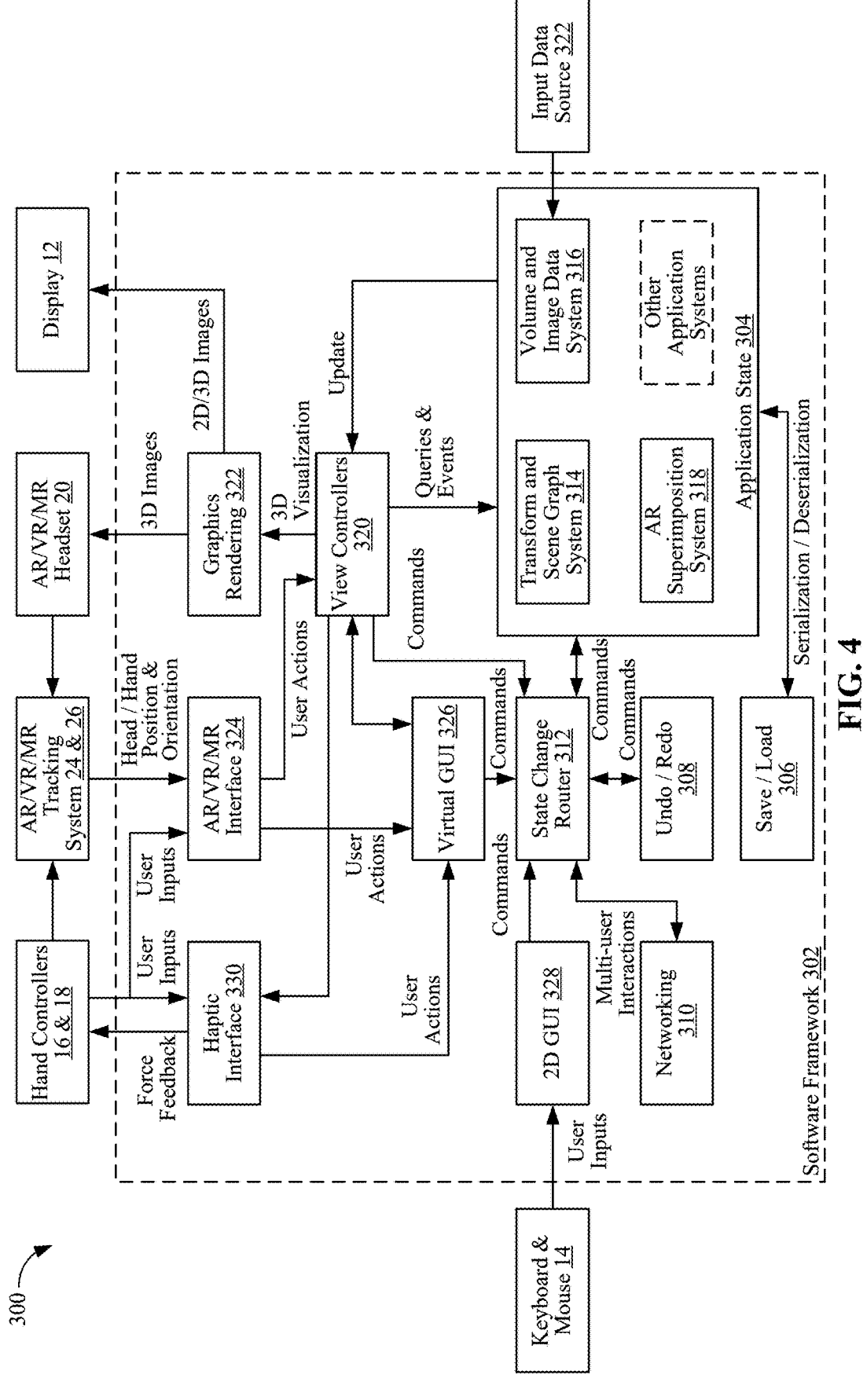
Figures 5, 6:
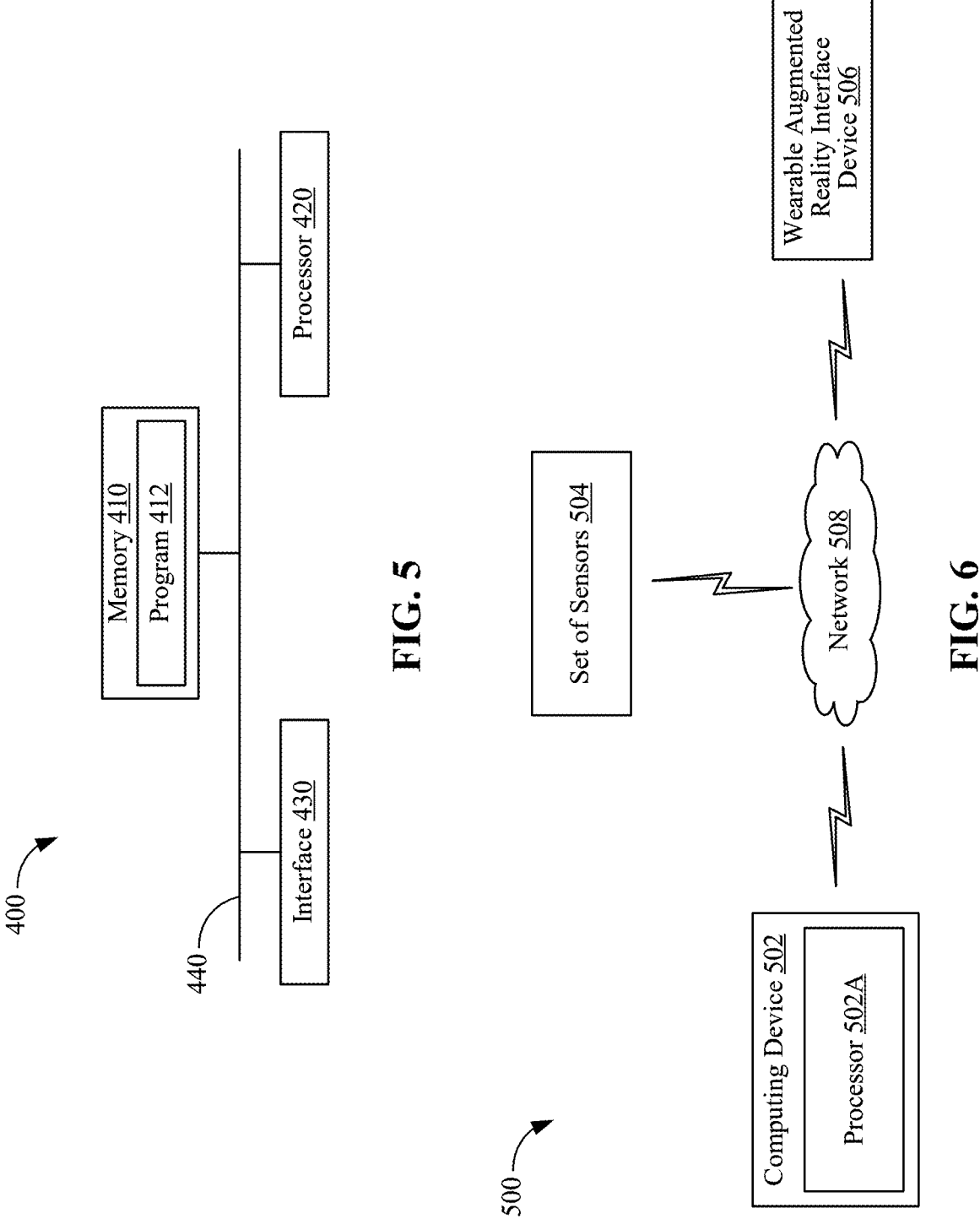

Having thus described example embodiments of the invention in general terms, reference will now be made to the accompanying drawings, which are not necessarily drawn to scale, and wherein:

FIG. 1 illustrates one example of a portable workstation in accordance with the disclosed technology;

FIG. 2 illustrates one example of a workstation in accordance with the disclosed technology;

FIG. 3 illustrates one example of a multi-user AR workstation in accordance with the disclosed technology;

FIG. 4 illustrates a block diagram of a software and hardware architecture for the workstations illustrated in FIGS. 1, 2, and 3;

FIG. 5 illustrates an example configuration of a computer or computing device suitable for use in the workstations illustrated in FIGS. 1, 2, and 3;

FIG. 6 illustrates schematic representation of the network environments implementing exemplary systems for rendering an operative guidance overlay in association with the patient, within the user's field of view, in accordance with an embodiment of the disclosure;

FIG. 7 is a flowchart that illustrates an exemplary method for spatially aligning the virtual anatomical model with the anatomical structure of the patient, in accordance with an embodiment of the disclosure;

FIG. 8 is a flowchart that illustrates an exemplary method for generating the guidance overlay data, in accordance with an embodiment of the disclosure;

FIG. 9 is a flowchart that illustrates an exemplary method for rendering the operative guidance overlay within the field of view of the user, in accordance with an embodiment of the disclosure;

FIG. 10 is a flowchart that illustrates an exemplary method for generating the guidance overlay data associated with the anatomical structure of the patient, in accordance with an embodiment of the disclosure;

FIG. 11 is a flowchart that illustrates an exemplary method for updating the virtual anatomical model of the anatomical structure of the patient, in accordance with an embodiment of the disclosure; and FIG. 12 is a flowchart that illustrates an exemplary method for rendering an operative guidance overlay, in accordance with an embodiment of the disclosure.

DETAILED DESCRIPTION

Embodiments are disclosed in the context of surgical planning and intraoperative visualization of patient-specific anatomy. However, in general, the embodiments may be implemented in or for any medical or surgical procedure utilizing a computing device for (i) acquiring volumetric imaging data of a patient's anatomy, (ii) automated segmentation of anatomical structures using artificial intelligence (AI), (iii) preoperative visualization and planning using augmented reality (AR), virtual reality (VR), or mixed reality (MR) technologies, (iv) spatially accurate alignment of virtual anatomical models over the physical patient in real time, and/or (v) real-time guidance for surgical incision planning, fracture reduction, or intraoperative navigation.

The presented technology relates to systems and methods for multidimensional data visualization, segmentation, and real-time interaction in an AR, VR, or MR environment. The disclosed embodiments generally apply to three-dimensional (3D) volumetric datasets from various imaging modalities, including but not limited to medical imaging, 3D simulation environments, and scientific volumetric data. In a medical setting, the disclosed embodiments enable a surgeon, physician, or clinician to rapidly load, segment, annotate, and interact with a patient's imaging scans in an immersive 3D environment. The user may interact with the segmented anatomical model as though manipulating a physical object-rotating, zooming, measuring, and simulating clinical maneuvers with precision and control.

In an augmented reality configuration, the technology enables the overlay of segmented anatomical structures onto the patient's physical body, accurately registered to real-world coordinates. The overlaid 3D images may correspond to anatomical regions of interest such as bones, muscles, lungs, soft tissues, or pathological sites, and may be visible even when such structures are occluded beneath the skin. The rendered overlays may further include virtual incision vectors, measurement annotations, and simulated hardware components (e.g., rib plates or surgical guides). In preferred embodiments, the system provides particular value for trauma or thoracic surgeries, where internal visualization of fractures or anatomical discontinuities is critical for minimally invasive procedures. Rendered visual cues may assist the surgeon by highlighting fracture boundaries, rib angles, insertion paths for surgical instruments, or depth indicators for incision guidance.

The medical imaging data used by the system may include scans from multiple modalities, such as computed tomography (CT), magnetic resonance imaging (MRI), CT angiography (CTA), MR angiography (MRA), Cone Beam CT (CBCT), and their post-processing outputs. The CT modality may produce cross-sectional 3D images of the patient's anatomy using X-ray signals, while the MRI modality may use magnetic fields and radiofrequency pulses to capture high-contrast images of soft tissues. CTA and MRA techniques, often involving contrast agents, may provide vascular detail. CBCT may be used in maxillofacial or orthopedic contexts for imaging of fine bone structures.

In addition to volumetric scans, the system may be applied to other multidimensional data sources, including digital radiography (DR), ultrasonography, or hybrid imaging systems. DR may generate two-dimensional X-ray projections used for anatomical referencing, while ultrasonography may provide real-time imaging of soft tissue and organ motion. These modalities may serve as supplementary inputs or contextual references within the broader planning and overlay framework.

The disclosed embodiments apply broadly across medical specialties where surgical precision and intraoperative anatomical awareness are paramount. These include, but are not limited to, thoracic surgery, orthopedic surgery, trauma surgery, spine surgery, neurosurgery, otolaryngology, cardiothoracic surgery, radiology, and general surgery. The technology supports clinical workflows in both preoperative planning and intraoperative execution, enhancing accuracy, reducing operative time, and improving outcomes.

In certain embodiments, the system utilizes volumetric anatomical representations constructed from geometric primitives referred to as "voxels", which are arranged within a three-dimensional volume. Each voxel is defined by integral-based (x, y, z) coordinates within a bounded spatial domain and occupies a regular cuboidal region. The system ensures non-overlapping voxel geometries and maintains a consistent spatial resolution to preserve the accuracy of the anatomical model. During a segmentation progress, individual voxels are assigned classification labels corresponding to anatomical structure types, such as bone, muscle, organ, or pathological tissue. The segmented voxels may be rendered with visual attributes, such as color, transparency, and outline enhancement, tailored to the clinical context. To automate voxel classification, the system employs artificial intelligence-based segmentation models, such as convolutional neural networks (e.g., U-Net, nnUNet, Swin UNetR), which are pertained and optimized for specific anatomical structures.

Furthermore, the system integrates real-time sensor data from a spatial tracking module to estimate the user's pose, detect motion, and perform dynamic registration of virtual models with the physical patient. The spatial tracking module may be implemented as standalone equipment deployed within an operating room or other clinical environment, or as an integrated component of other devices, including but not limited to an AR head-mounted display, a surgical navigation system, or a surgical light. To mitigate latency and maintain stability of the operative guidance overlay, the system employs predictive algorithms, such as Kalman filters. The resulting augmented reality visualization is continuously updated in response to the surgeon's movements and changes in surgical perspective, thereby supporting a seamless and responsive operative guidance experience.

FIG. 1 illustrates one example of a portable workstation 10 in accordance with the disclosed technology; FIG. 2 illustrates one example of a workstation 110 in accordance with the disclosed technology while FIG. 3 illustrates one example of a workstation 210 with an Augmented Reality configuration of the disclosed technology. In the illustrated examples, the workstations 10, 110 and 210 may include one or more AR/VR/MR devices, which along with the data visualization and interaction discussed herein provide several advantages previously unattainable in the art.

Referring to FIG. 1, the workstation 10 includes a computer 11, a display screen 12, a set of keyboard and mouse 14. The workstation 10 is shown being provided on a compact wheeled carrier 104, making the workstation 10 easily transportable. The workstation 10 is shown being operated by a user 2. In the illustrated example, the user 2 is wearing an AR/VR/MR headset 20 for viewing a stereoscopic visualization 30 of one or more sets of 3D volume data or 2D image data input into the workstation 10 and rendered by the workstation 10 in accordance with the disclosed principles. In the illustrated embodiment, a rendering of one or more 3D volume datasets or 2D image datasets in accordance with the disclosed principles may also be presented on the display screen 12.

The AR/VR/MR headset 20 helps in viewing one or more anatomical structures by the visualization 30 of one or more sets of 3D volume data or 2D image data. The visualization 30 may be in 2D or in 3D and may be viewed from different angles and positions. The visualization 30 of one or more anatomical structures may be projected onto the actual patient which the data was previously scanned from. The visualization 30 may be superimposed with the corresponding actual anatomical structures by collocating the 3D volume data or the 2D image data with the patient body.

The AR/VR/MR headset 20 may be connected to the workstations 10, 110 for receiving and conveying the data. Said connection may be achieved by one or more universal serial buses (USB) or display cables. The connection may also be established network connections between the workstations 10, 110 and the AR/VR/MR headsets 20, which have standalone computation and communication capabilities. The network connection may be a local area network such as Wi-Fi network, or a high speed and low latency wide area network such as 5G cellular network or fiber broadband network.

The user 2 is also shown wearing a headphone 22 for listening to auditory simulations as the user 2 observes and interacts with the volume or the image data input into the workstation 10. In the illustrated example, the user 2 is operating two hand controllers 16, 18 also used to interact with the data rendered by the workstation 10 in accordance with the disclosed principles.

Referring to FIG. 2, the workstation 110 includes a computer (not shown), a display screen 12, a set of keyboards and mouse 14. The workstation 110 is shown being operated by the user 2 at a desk 4 or other workspaces. As explained below in more detail, due to the novel multidimensional data visualization and interaction provided by the disclosed principles, patient-specific data is easily loaded into, rendered, and interacted with in both workstations 10, 110 making the workstations 10, 110 suitable for viewing critical scan information in all areas of health care facilities, including but not limited to a radiology lab, an operating room, an emergency room or a doctor's office. The workstations 10, 110 may also be suitable for patient education and engagement. Patients may be able to better understand their condition and physicians may walk the patients through proposed interventions, actively consulting with them to determine the best therapeutic choice for their respective situations. This may reduce patient anxiety and reinforce the patients understanding of their treatment and increase informed consent for medical plans of action.

Referring to FIG. 3, the workstation 210 includes a computer 11, such as a desktop PC or laptop, an spatial tracking system 34 connected to the computer 11 for reporting positions of physical objects of significance, and a network router (not shown) for connecting the computer 11 with one or more AR headsets 20 and other devices as needed, such as the spatial tracking system 34. Other input and output devices, such as the display screen 12 and the keyboard and mouse 14 are available for the user 2 to interact with the workstation 210 via graphics user interfaces (GUI). Some examples may include the workstation 210 operating in communication with a remote device. Examples of the remote device may include, but are not limited to, a handling device (such as a print head controller and a marking engine), a storage medium, a computing device, and a printer. The remote device may be configured to receive, store, process, display, email, and/or print images and 2D or 3D software models.

In an embodiment, the spatial tracking system 34 may be implemented as a separate device that is physically connected to the computer 11. In another embodiment, the spatial tracking system 34 may be implemented as a software component configured to receive input data from existing sensors integrated within the AR headset 20 or other components of the workstation 210. The spatial reference markers 36 are operatively configured to interact with the spatial tracking system 34 to enable determination of position and/or orientation of an associated object using optical, electromagnetic, or other sensing modalities. The modality of spatial reference markers 36 may vary depending on the fiducial system employed by the spatial tracking system 34. In certain embodiments, the spatial reference marker 36 comprises one or more of: a passive visual marker, a light-emitting optical marker, an electromagnetic marker, or any combination thereof. In further embodiments, the passive visual marker comprises one or more of: a constellation of spheres or other geometric primitives, a two-dimensional (2D) bar code such as a QR code or an AprilTag, a constellation of multiple 2D bar codes, a 2D image, a three-dimensional (3D) object, or any combination thereof.

The spatial reference markers 36 may be attached to one or more physical objects of significance and/or one or more AR headsets 20 to track their real time position and orientation. In the illustrated embodiment, the physical objects of significance may include patient anatomy 32, a fixture attached to the patient anatomy, a patient support structure, such as an operating table, or one or more surgical instruments 38. Custom attachments may be used to connect the spatial reference markers 36 to objects of significance. In a medical environment, such attachments may include custom-designed components manufactured by additive or subtractive process, configured to couple to a fixture on a patient's body 32, or directly to the patient anatomy such as skin or bone. In certain embodiments, the spatial reference markers 36 may alternatively be affixed directly to the anatomy using adhesive or other suitable means. Similar attachment or affixing methods may also be employed on AR headsets 20.

The workstation 210 is shown being operated by one or more users 2. In the illustrated example of FIG. 3, each user is wearing an AR headset 20, which is a transparent visor with an onboard computer that allows the user to see 3D images overlaid over the real world. The AR headset 20 presents to the user 2 a stereoscopic visualization 30 of one or more 3D objects and/or one or more 2D images. The spatial tracking system 34 reports the position and orientation of all the spatial reference markers 36 that it observes to the workstation 210. The offset between each spatial reference marker 36 and the associated object of significance may be predetermined based on the attachment geometry or may be derived from tracking data during operation. Similarly, the view perspective of the user 2 may be computed based on the tracked position and orientation of the AR headset 20 as well as the offset between the headset and user 2's both eyes. The workstation 210 uses these offsets to draw each rendered object in the correct location from the view perspective of the user 2, allowing the stereoscopic visualization 30 of the 3D objects or 2D images to be superimposed to their real-world counterparts, which may be the patient's body 32, one or more surgical instruments 38, or one or more spatial reference markers 36.

FIG. 4 illustrates a block diagram of a software and hardware architecture 300 for the workstations illustrated in FIGS. 1, 2 and 3. In the illustrated example, the architecture 300 includes interconnected devices and logic that are integrated by a software framework 302. The software framework 302 includes an Application State module 304 which maintains one or more virtual scenes. Each virtual scene may be a distinct state of the application that contains all data and content presented in AR/VR/MR environment. The Application State module 304 further comprises one or more application systems and system data. Each application system has corresponding system data, and each system data has a corresponding application system. The Application State module 304 maintains all application systems and the system data associated therewith for lifetime of the application. The Application State module 304 allows querying and interaction with any of the application system and the system data associated therewith in a specific and controlled manner. Each application system includes logic for creating, modifying, and destroying the corresponding data and serves as a target for all application commands. The application system also includes a public interface that allows querying current events and subscribing to an event that is called whenever the system data is created, modified, or destroyed. The changes made in the data may be preserved even after the user 2 leaves the scene.

The application systems comprised in the Application State module 304 may include a transform and scene graph system 314, a volume and image data system 316, an AR superimposition system 318, and plurality of other application systems that define application-specific features and user interactions.

The software framework 302 further comprises a Save/Load module 306 for saving and loading operations. The saving operation serializes all application systems and the system data associated therewith in the Application State module 304 of an active session, including one or more original, processed, or edited volume or image data, their surface representation, as well as results of the user interactions, and saves into external files. The loading feature loads complete set of data from a file, deserializes the data and then initializes the Application State module 304 as well as all relevant application systems and system data. In a desired embodiment, saved data may be saved in a portfolio of files with a unique file extension, so the loading process can identify the files by such file extension.

The Save/Load module 306 further comprises functionalities for converting surface representation of original, processed, or edited volumetric or image data into polygon mesh model files, which are then stored in the file system. In certain embodiments, the polygon mesh models may be saved in one or more formats, including STL, OBJ, 3MF, or GLB.

The software framework 302 includes a State Change Router 312 that serves as a hub of the application commands. Application commands may describe the creation, modification or destruction of the system data corresponding to one or more application systems. Application commands may be received from the user interactions through graphics user interfaces (GUIs), such as the virtual GUI 326 or 2D GUI 328, or from command issuers, which may be View Controllers 320, an Undo/Redo module 308, or a Networking module 310. Upon receiving the commands, the State Change Router 312 further sends them to command listeners, which may be plurality of application systems in the Application State module 304, the Undo/Redo module 308, or the Networking module 310 and/or a 3D Printing module (not shown).

The software framework 302 further comprises the Undo/Redo module 308 for undo and redo operations. The Undo/Redo module 308 receives new application commands from the State Change Router 312 and stores the commands in a command stack for undo and redo operations. The undo operation reverses the user interaction and recovers the system data at a previous state; the redo operation reverses an undo operation and recovers the system data at a state prior to the undo operation.

Features and operations in the plurality of application systems are implemented by performing a plurality of low-level operations on the system data. To group low level operations into a single logical high-level operation, all tools perform the operations on a context object which may be first acquired from the State Change Router 312. This also serves as a locking mechanism to prevent multiple tools from modifying the one or more system data in unpredictable ways.

Each low-level operation may be implemented as a command that records the before and after states of its execution. When a tool performs operations, the context records a list of all the commands that have been executed by the current tool. When the tool is finished making changes, it releases the context to finalize its changes. The context bundles the low-level operations into a single high-level undo/redo operation so that when the user 2 triggers the undo feature, all changes made by the last tool will be reverted, even if they consist of multiple sub-commands. Once the high-level undo/redo command is assembled, it is added to a stack of previous undo-redo commands. Operations may be undone and redone by applying the appropriate state from each command. The undo/redo stack can also be serialized and saved to disk, both to support resuming a session, but additionally as a record of all the steps taken in the planning session.

The software framework 302 further comprises the Networking module 310 which supports multi-user interaction and collaboration over the network. The Networking module 310 sends the multi-user interaction data or commands from the State Change Router 312 to other users on a network. The Networking module 310 also receives the interaction data from the other users and sends it to the State Change Router 312 to modify the data held by the Application State module 304 on behalf of a remote user. In some examples, the Networking module 310 may operate in communication with the remote device over a network, such as network 502.

The Networking module 310 may allow multiple users to share and synchronize the entire Application State module 304, all application systems and the system data associated therewith, as well as the undo/redo stack, so multiple users may interact with the same volume objects in their own AR/VR/MR environment. Any user may be able to view and interact with one or more volume or image data, and see the changes made by others applied locally. In one embodiment, a voice/chat feature may be provided to allow users to communicate directly. The network connection may be over a local area network or a wide area network such as the Internet.

In the illustrated embodiment, the software framework 302 includes a plurality of View Controllers 320 for visualizing the system data to the user 2 as a plurality of 3D objects, 2D objects, or graphical user interfaces (GUIs) and giving the user means to interact with the 3D/2D objects and their underlying data. The plurality of View Controllers 320 is in place for querying the public interface of the Application State module 304 for the state of one or more application systems, subscribing to events that will trigger if the data changes, and issuing the commands to create, modify, or destroy the system data based on the user instruction with plurality of interaction features. The plurality of View Controllers 320 issue the commands through the State Change Router 312. In an embodiment, the plurality of View Controllers 320 may send the command in a direct mode or an indirect mode through the virtual GUI 326 to the State Change Router 312.

In the illustrated embodiment, the software framework 302 may include the AR/VR/MR interface 324 for interfacing with the AR/VR/MR hardware, including one or more AR/VR/MR tracking system 24, 26, AR/VR/MR headsets 20 and hand controllers 16, 18 worn or operated by the user 2. The AR/VR/MR interface 324 receives the positions and orientations of user's head or hands, as well as all user inputs from hand controllers 16, 18. In a desired embodiment, the AR/VR/MR tracking system 24, 26 may track the pose of user 2's hands and further recognize hand gestures, which may trigger user actions. Said user inputs and actions are used to update the virtual GUI 326 and interact with plurality of View Controllers 320.

It should be understood that, although the present example illustrates the use of one or more AR/VR/MR tracking system 24, 26 employing tower-based outside-in tracking, such implementation is not intended be limiting. In other embodiments of the present disclosure, interfacing with the AR/VR/MR hardware may be achieved using inside-out tracking techniques that do not require external towers.

The software framework 302 further includes the graphics rendering module 322 which renders the visualization of the system data from all application systems as images captured from one or more specific viewpoints. The graphics rendering module 322 receives the system data through the plurality of View Controllers 320 and visualizes the data on one or more 2D planes or in a 3D space via plurality of graphics rendering mechanisms.

The graphics rendering module 322 may provide plurality of camera nodes that compute the correct viewer-centered perspective projection on virtual projection planes. In an embodiment, the graphics rendering module 322 may stereographically render a view of the Application State on the AR/VR/MR headset 20. The rendering perspective may be consistent with a physical position and an orientation of the AR/VR/MR headset 20. The graphics rendering module 322 may properly render both left and right views according to the position and orientation of the user's head given by the AR/VR/MR interface 324. The graphics rendering module 322 is performed by the graphics processing units; the rendering results may be presented on the display screen 12 and the AR/VR/MR headset 20 and may be reproduced on the 2D GUI 328 or the virtual GUI 326, which may be presented on the display screen 12 and the AR/VR/MR headset 20.

The graphics rendering module 322 further includes a remote rendering technique which uses the computer 11 of the workstation 210 to render the images based on the view perspective of the AR/VR/MR headset 20, and send them to the headset 20 to draw in front of the user's eyes. With a more powerful graphics processing unit and larger memory, the remote rendering technique may provide images of far greater 3D resolution and visual fidelity than is typically possible with modern standalone AR/VR/MR headsets 20, which have limited computational power onboard (roughly equivalent of a modern cell phone).

A common challenge in all applications of remote rendering is the latency between a user performing an action and having it represented in the images. In the case of the presented technology, the displayed image is dependent on the position and orientation of the user's head, but it takes time to render the image, send it to the headset 20, and display it, while the user's head may have minor though constant movement and rotation. The nature of augmented reality makes it more important than usual to solve the issue, as the latency can be disorienting. For example, if the user was looking at a rendered object and steps to the left, the object would appear to be stuck to their head and move left with them for a brief moment, before sliding back where it belongs.

To solve this, the graphics rendering module 322 further implements a depth-based spatial latency compensation system, similar to the asynchronous space warp techniques used in spatial computing. When the workstation renders the 3D images, it also renders a "depth map," or a texture that stores the distance of every pixel in the images to the camera. This is sent to the headset 20 along with the color images. The headset 20 then draws the images on a plane, then uses tessellation to efficiently split the plane into many very small pieces, and slides each piece backwards based on the values from the depth map. This recreates the 3D shape quite closely from the rendered object viewed from the front, but importantly, user can view it from slightly different angles and the object still appears to be shaped correctly. The headset 20 then uses the timestamp of the image to move that plane to where the image was taken, which is where the headset 20 was a few milliseconds prior. Other than some minor disocclusion artifacts, this results in an up-to-date version of the old image from the new angle.

In addition, the graphics rendering module 322 may further compress and decompress the stream of images to minimize the time it takes to send the images from the workstation 210 to the AR headset 20 over the network. Both devices handle the compression/decompression using dedicated hardware to minimize latency. In one embodiment, the hardware acceleration of the Advanced Video Coding, which is also referred to as H.264, is implemented on both the workstation 210 and the AR headset 20.

The software framework 302 further incudes one or more graphics user interface (GUI) to facilitate the user 2 to interact with the software. In the illustrated embodiment, the virtual GUI 326 is presented in the virtual scene and interactable via AR/VR/MR headsets 20, hand controllers 16 & 18, user's hand movements, gestures, or user's eye movements. The illustrated embodiment further includes one or more 2D GUIs 328 that are presented on the display devices 12, and interactable via keyboard and mouse 14, or the touchscreen. User interactions via the GUIs may trigger commands which change the state of the application.

The software framework 302 further includes the haptic interface 330 for mediating communication between the user 2 and the computer 11, monitoring the position, orientation, velocity, and acceleration of user's hand from, for example, joysticks and/or hand controllers, and applying force feedback, i.e., haptics, to the user's hands via the joysticks and/or the hand controllers 16, 18. The haptic interface 330 generates force output directly to simulate a field of force or other mechanical effects such as gravity, friction, damping, or vibration.

The haptic interface 330 sends the input data from the joysticks and/or the hand controllers 16, 18 to the virtual GUI 326 and/or the plurality of View Controllers 320. The haptic interface 330 links the joysticks and/or the hand controllers 16 with the virtual tool that further drives the plurality of View Controllers 320 to interact with the Application State module 304 and modifies the system data. The haptic interface 330 may also indirectly interact with the plurality of View Controllers 320 through the virtual GUI 326.

The graphics rendering module 322 may implement a variety of visualizations of the volume or image data either on a 2D plane and/or in a 3D space, including but not limited to a plurality of shaded surface display (SSD) techniques, a plurality of volume rendering techniques (VRT), a plurality of multi-planar reconstruction (MPR) techniques, and a plurality of intensity projection techniques such as the maximum intensity projection (MIP) technique.

In one embodiment, the graphics rendering module 322 may implement the visualization via a plurality of shaded surface display (SSD) techniques which reflect the structures of interests by visualizing the surface representation of a volume layer generated by the volume meshing process. The volume layer is a set of geometry that shares the same rendering material and source. It may be constructed either from an iso-surface contained in a scalar volume dataset, a signed distance field (SDF) of an editable volume object, or a binary volume dataset derived from volume segmentation. Multiple iso-surface layers may be created from the same volume dataset.

The rendering of layers as geometry allows seamless multi-modality rendering. Segmentation or iso-surface layers can be mixed and matched from different scan modalities. The layers from every loaded medical imaging dataset faithfully represent the patient specific anatomy in virtual reality; they can also be accurately superimposed with the actual patient in an augmented or mixed reality environment. As an editable volume object is modified, the associated surface representation may be updated in real-time.

The graphics rendering module 322 may also implement an order-independent transparency (OIT) method which may be used to render an arbitrary unsorted polygons with correctly sorted transparency. This allows displaying the multiple volume layers and other 3D or 2D geometries with adjustable and correct transparency. Applying the OIT method, the opacity of each layer or geometry can be adjusted independently from fully opaque to fully hidden or anywhere in between. In a desired embodiment, the OIT method is implemented using an A-Buffer technique with a per-pixel linked list. As the anatomy is being rendered, the fragments are accumulated in these lists instead of directly composited to a frame buffer. At the end of a frame, the lists are sorted by depth, blended, and then composited with an opaque part of the scene.

It should be appreciated that a plurality of rendering features may be available. At both design time and runtime, the rendering features may be toggled on or off, or have their parameters changed. These features may include, but are not limited to, per-layer colors and transparencies, photo-realistic rendering, diagrammatic cutaways, soft deformation in response to touch, and X-ray visual simulation. In one embodiment, two lighting options may be available: a point light without distance attenuation attached to a camera, and an image-based lighting scheme with directional occlusion. In addition, the meshes may be exported for use in an external software.

The display outputs, from both the 3D and 2D renderings, may be presented on both the AR/VR/MR headsets 20, and the regular computer displays 12 such as monitors, projectors, or televisions. To generate the display outputs on the AR/VR/MR headsets 20, two scene cameras are set to move and rotate based on the positions and orientations of user's head, as well as the Inter Pupillary Distance (IPD) of user's eyes. Stereoscopic vision and depth perception are therefore achieved via the difference of the display outputs for both eyes. On regular computer displays 12, the display output can either be the clone of one of the outputs to the AR/VR/MR headsets 20; optionally, for better experience of the surrounding audiences, the output can be obtained from a separated scene camera which may stay at a fixed point in space, or follow the perspective of the user 2 while keeping the camera movement smooth and steady.

In a desired embodiment, the plurality of volume rendering techniques may include a novel rendering technique referred to herein as a view-ray-ordered volume rendering technique. For visualization of end-user provided volume data, the workflow may be as follows: First, unnecessary structures are eliminated. To do so, the user 2 outlines a 2D region of interest on a maximum intensity projection image of the volume data about any voxel-aligned axis. This 2D region is projected into a 3D polyhedron constrained by the AABB of the one or more volume object, and any information outside of the 3D polyhedron is discarded. Next, a transfer function is specified, aided by an interactive 3D visualization. The transfer function includes one or more iso-values defining the iso-surface of interest, as selected on a data-value histogram of the one or more volumes. The transfer function furthermore includes scale and bias values that modulate a gradient magnitude driven color ramp. The color ramp tends to distinguish softer versus harder materials. Finally, opacities corresponding to the two extrema of a color ramp may be modified and rendered with exact transparency. All transfer function changes reflect immediately on the 3D rendering. Details are rendered with sub-voxel interpolated details.

The plurality of volume rendering techniques may also include a direct volume ray-caster technique, which renders multiple iso-surfaces, or an SDF obtained from the volume data by marching the ray though the one or more volume object and evaluating intersections with the surfaces. It supports multiple iso-surfaces at different scalar values, with correct transparency, and optionally participating medium rendering. Participating medium rendering simulates increasing opacity as the material gets thicker. Each surface can have different material settings, which may include but not limited to color, opacity, and density for the internal material.

The graphics rendering module 322 may also implement a plurality of MPR techniques to reconstruct a visualization of one or more volume datasets on one or more intersecting 2D planes. The scalar value at each pixel of the plane can be determined by trilinear interpolation of the voxel values of the containing voxel cell in a volume grid. The MPR can be rendered in greyscale or pseudo color with fully configurable mapping of the colors with the voxel values. Transparency can be set along with the color mapping to allow viewing of the 3D rendering behind the MPR overlay, or making certain portion, such as the space outside of the region of interest, less noticeable or even invisible.

The graphics rendering module 322 may also implement a plurality of intensity projection techniques to visualize one or more volume datasets on a 2D plane by projecting all voxels of the volume datasets into a single 2D image. Each pixel of this 2D image is a combination of all projected voxels. According to different methods by which the projected voxels are combined, the plurality of intensity projection techniques may comprise a maximum intensity projection (MIP) technique, a minimum intensity projection technique, an average intensity projection technique, a median intensity projection technique, a standard deviation intensity projection technique, and a cumulative intensity projection technique.

As discussed above, in one or more embodiments in which the one or more haptic devices are being used, the haptic interface 330 may allow interactions between the virtual tool corresponding to the joysticks and/or the hand controllers 16, 18 and elements within the virtual scene. A haptic proxy is maintained to describe the position of a haptic interface point, which tends to move towards the actual position of the haptic stylus while always staying outside of any haptic-enabled objects. Each object may be assigned with different haptic materials, including but not limited to stiffness, viscosity, static friction, and dynamic friction, as well as a plurality of physical properties such as density, gravity, elasticity, damping, etc. Therefore, the user 2 may perceive a life-like tactile feedback on different surfaces and textures when touching haptic-enabled objects.

In one or more embodiments in which the joysticks and/or the hand controllers 16, 18 are being used for providing haptics, the haptic interface 330 may track the events of haptic interaction, including the beginning of contact, the end of contact, continuous contact, penetration, to name a few. Custom behavior may be programmed when the events are triggered. The haptic-enabled objects may be configured to be penetrable, and the objects may be penetrated through when the force user applies to the surface of the objects exceeds a predetermined threshold.

In one or more embodiments in which the joysticks and/or the hand controllers 16, 18 are being used, the haptic interface 330 may implement one or more spatial constraints to the haptic interaction point, which may limit the DOF of the translation and/or rotation of the virtual stylus. The haptic interface 330 may also implement programmable custom haptic force effects, including but not limited to a constant force, a viscosity effect, a vibration effect, or a magnetic effect.

In accordance with the disclosed principles, and in one or more embodiments in which the joysticks and/or the hand controllers 16, 18 are being used for haptics, the architecture 300 may support, via the haptic interface 330, the haptics interaction with volume layers, which may allow the user 2 to touch and interact with one or more volume layers via the joysticks and/or the hand controllers 16, 18. For each volume layer, a subset of voxels near the moving path of the haptic proxy may be collected. An iso-surface within this subset of voxels may be computed and used to determine a new position for the haptic proxy. Multiple iterations of this process may be executed within the frame to refine the proxy position. Based on the offset between haptic proxy and the actual stylus position, as well as all haptic properties applied to the volume layers, an output force may be calculated and applied to the joysticks and/or the hand controllers 16, 18 as the tactile feedback of the volume layers. The haptics interaction may also work with editable volume objects, whose data and surface representations may be modified in real-time to simulate the change of geometry such as drilling, cutting or augmentation.

In accordance with the disclosed principles, the AR/VR/MR interface 324 may be designed and implemented to provide compatibility with various AR/VR hardware. Specifically, the AR/VR/MR interface 324 may identify AR/VR/MR devices (i.e., the AR/VR/MR headset 20 and the hand controllers 16, 18) upon startup of the application and may map the correct inputs and outputs for the headset 20 and the hand controllers 16, 18 being used. In a desired embodiment, world-based user interfaces and custom-built hand models may be implemented into the architecture 300 such that each user may receive a consistent experience even though different AR/VR/MR headsets 20 or the hand controllers 16, 18 are being used. The AR/VR/MR interface 324 may support dominant and secondary hand references, allowing the architecture 300 to switch from right-handed mode to left-handed mode at any time. In the disclosed embodiment, the user's hands may track any volume layer or any 3D/2D geometry in the virtual scene via distance tracking. The tracking does not need to be dependent on any collision bounds, allowing more accurate interaction with small objects that are in proximity.

In a desired embodiment, the AR/VR/MR interface 324 includes the virtual GUI 326 designed specifically for being used in conjunction with the one or more volume layers and other 3D/2D geometries in accordance with the disclosed principles. Being anchored to the wrist may allow the virtual scene to be scaled up many times its original size and let the user 2 observe the volume layers or geometries from the inside. Icons and tags of the UI buttons may be rendered in a depth-independent manner, allowing the user 2 to see the buttons even when standing inside a solid volume layer. The virtual GUI 326 may also be easily moved or hidden to avoid obstructing the view.

As noted above, the Application State module 304 may comprise the transform and scene graph system 314 which maintains a data structure that holds the transformational relationships, such as translation, rotation, and scale factors, among all elements in the virtual scene. The data structure may maintain a transformation hierarchy that describes a relation of transformations of scene elements with each-other. The transform and scene graph system 314 may be organized around parent-child relationships via a tree structure with the origin of the global coordinate system being the root and each element in the virtual scene being represented as a node. The position, orientation and scale factor of each node may be defined by the transformation matrix, and the transformation matrix of a parent node is applicable to all its descendant nodes. Multiple tree structure may be simultaneously maintained by the transform and scene graph system 314 to reflect different states of the same set of system data, allowing the user 2 to view any certain state and/or compare between states. In a desired embodiment, multiple scene graphs may be organized to represent the patient anatomy at distinct phases of surgery, such as a preoperative phase, a plurality of the intraoperative phases and a postoperative phase.

The Application State module 304 may also comprise the volume and image data system 316. The volume and image data system 316 receives one or more 3D volume datasets or 2D image datasets generated or maintained by the input data source 322 which may be a medical scanner. Examples of medical scanners that may be used as the input data source 322 for characterizing the physical objects include, but are not limited to, the computed tomography (CT) scanner, the magnetic resonance imaging (MRI) scanner, the digital radiography (DR) scanner, or the ultrasound scanner, such as those typically used for obtaining the medical images. The input data source 322 may also be a database such as the Picture Archiving and Communication System (PACS), which provides economical storage and convenient access to images from multiple modalities.

The volume and image data system 316 may input the 3D volume data or 2D image data supplied in either a Digital Imaging and Communications (DICOM) format or an MHD/RAW format. The volume or image data with 16-bit and 8-bit integer values may be directly supported; other formats may be automatically converted to 16-bit. To accommodate distinct types of the input data sources, the data contents of scalar 3D volumes (such as CT or MRI scans), or 2D images (such as DR or ultrasound scans), as well as the binary volume or images from the segmentation of the scalar datasets may be processed and maintained by the volume and image data system 316.

The volume and image data system 316 may implement a volume meshing process which generates surface geometries from iso-surfaces across the one or more volume objects while sufficiently performant as to allow constant real-time alterations of the editable volume datasets and their corresponding surfaces. Based on the surface nets algorithm, it may be able to infer and generate a variety of sub-voxel geometric features from a trilinear interpolation function, including the disambiguation of what would otherwise be non-manifold portions of the surface. This is particularly evident in the visualization of a thin or a tunnel-like structure. Surface normal may also be generated for use in lighted rendering, in such a way as to automatically produce an appropriate mixture of hard edges and curved surfaces to satisfyingly represent complex edges without the appearance of undue darkness or obvious facets.

The volume and image data system 316 may also implement a topological smoothing process intended to be used in combination with the volume meshing process, which produces a smoother mesh from the one or more volume object of binary segmentation without overly deviating from the original geometry. Because the topological smoothing process takes place before regular meshing, the smoothed mesh and scalar data are self-consistent, and the system's output is fully and transparently compatible with any volume-manipulating features and can be trivially converted back into the original binary segmentation. The smoothing computation takes place partially on a Graphic Processing Unit (GPU).

The volume and image data system 316 may also implement a series of post processing algorithms of noise reduction to improve the visual fidelity of volume or image visualization. The edge and feature preserving smoothing algorithm may be executed upon the one or more volume or image datasets to suppress low-amplitude noise across all frequencies and make voxels or pixels of the same material cluster closer in a scalar value. Upon the output of the smoothing algorithm, the algorithm of small isolates culling may be executed to remove additional noise by replacing topologically isolated small fragments within the one or more 3D volume datasets or 2D image datasets with smoothed data. Upon the output of the small isolates culling algorithm, a deconvolution algorithm may be executed which simultaneously hardens edges or corners, and smooths where no edge or corner exists. Thus, the influence of a point spread function is removed, voxels or pixels of the same material cluster closer together in the scalar value, and the remaining fragments of noise become more topologically isolated. Upon the output of the deconvolution algorithm, the small isolates culling algorithm may be executed again thus, topologically isolated small fragments that were not identified in the first execution of the algorithm may be replaced with the smooth data.

According to the disclosed principles, the number of segmented volume objects produced from a same source volume object may optionally be recombined into a single volume object having auxiliary layer ID voxels. A layer ID may be used to simulate a single object consisting of distinct, interconnected materials. In addition to, or alternatively, the segmented volume objects may be cropped to an Axis-Aligned Bounding Box (AABB) containing existent voxels, while retaining position information. In addition, or alternatively, the number of segmented volume objects produced from the same source volume object may be individually cropped to the AABB of the union of their existent voxels. In one embodiment, the segmented volume objects are converted to scalar volume objects via a topological smoothing process.

The volume and image data system 316 may also implement a volume editing process which allows the one or more editable volume objects and the one or more surface representations associated therewith to be modified in real-time or separated into the multiple independent segments. The area being edited may be specified by either the signed distance function (SDF) or a connected component labeling (CCL) process.

The signed distance function (SDF) is a mathematical function that can return the signed distance from the cut boundary to any point in the one or more volume objects. The SDF may include but is not limited to a plane, a geometric primitive which may be a cuboid or a sphere, or a manifold mesh. The editing modifies the original one or more volume objects to reflect the remaining part, and if needed, generates the additional volume objects for the newly cut segments. The region of interest for the editing, which is conservatively defined as any cuboidal area that could contain all voxels being modified, may define the size and dimension of the new volume objects. The voxel values from that area are copied from the original volume data. To construct the cut hollow surface in the original one or more volume objects and the solid surface in the new ones, the signed distance function shall be applied to every voxel in the region of interest in the original one or more volume objects, and then applied in the new one or more volume objects but with the distance sign reversed. The new signed distance value at any voxel shall be the minimum of the original value and the distance returned from the function.

In a desired embodiment, user may define one or more SDFs through auxiliary 3D shapes introduced via user interaction. In another desired embodiment, the volume cutting feature further comprises a paint to separate a mode adapted to define cut regions by gradually painting on one or more editable volume objects by a virtual paint bush of various shapes and dimensions. The area to be separated may be rendered with highlighting visual effects for the user 2 to preview the cut regions before cutting.

The connected component labeling (CCL) is a process which uniquely labels all subsets of the voxels whose represented geometries are connected. The volume editing may be achieved by breaking such connectivity with one or multiple mesh based cutting boundaries defined by the user 2. In an embodiment, the editable volume system may further utilize the CCL process adapted to detect the separation of the one or more volume objects and the surface representation associated therewith. In another embodiment, the CCL process may be adapted to detect whether a cut specified by the user 2 may successfully separate the one or more editable volume objects, and the forecast of the cutting results may be presented to the user 2 before the cut is finalized.

One or multiple new editable volume objects may be generated to describe the newly separated subsets of voxels, with the voxel values copied from the original one or more editable volume objects. To construct the newly cut surfaces resulted from user defined cuts on both the original and new editable volume objects, the values of the voxels in all voxel cells that intersect with the boundary mesh shall be modified according to the minimum distances between the voxels and the cut surfaces.

To update the 3D rendering of the editable volume objects, volume meshing may be re-executed once volume editing is completed. The user 2 may have multiple options to interact with the newly generated volume objects. These interaction features may include removal, maneuver, and various measurements.

The volume and image data system 316 may also implement a volume ray casting process, which may effectively and accurately calculate the first point where a given ray intersects with an iso-surface of a volume dataset, or a signed distance field of an editable volume object. This functionality facilitates other volume operations including ray casting and collision detection.

As noted above, the Application State module 304 may also include an augmented reality (AR) superimposition system 318 configured to overlay visualizations of a virtual scene onto real-world objects while preserving relative rotations and translations. A user 2, such as a trained professional, may register one or more 3D volumes, 2D images, or 3D geometries with virtual objects representing spatial reference markers 36 within the virtual scene. The spatial reference markers 36 may be physically attached to real-world objects of significance, corresponding to their digital counterparts registered in the virtual environment. When an AR headset, or a VR/MR headset with camera passthrough functionality, is utilized, multiple tracking techniques may be employed to detect the real-time 3D position and orientation of the spatial reference markers 36, enabling accurate overlay of their virtual representations. Using the transformational matrices maintained within the transform and scene graph system 314, the remainder of the virtual scene is correctly superimposed onto real-world counterparts when displayed through the AR/VR/MR headset 20. When one or more real-world objects bearing spatial reference markers 36 are moved, all corresponding virtual objects are automatically repositioned to maintain accurate superimposition. In certain embodiments, the real-world objects registered with spatial reference markers 36 may include a patient's body 32, a fixture attached to the patient's body, a patient support structure such as an operating table, or one or more surgical instruments 38.

In some embodiments, one or more real-world objects, which may be anatomy structures within a patient's body, may be partially or completely obscured by external objects. The AR superimposition system 318 may reveal such internal structures by displaying their virtual counterparts in alignment with the real-world context. In other embodiments, the superimposed virtual objects may represent a state different from the real-world objects, such as preoperative anatomy versus surgical planning. This capability enables visualization of differences between multiple states and provides operative guidance for actions to be performed, including surgical procedures.

As noted above, the plurality of View Controllers 320 may issue commands to create, modify or destroy the system data of different application systems. A plurality of interaction features may be implemented by specific application systems and corresponding view controllers. Said interaction features may comprise one of more of the following: 1) a spatial tracking feature; 2) a user maneuver feature; 3) a volume editing feature; 4) a measurement feature; 5) a snapshot feature; 6) a 3D visualization feature; 7) a 2D visualization and overlay feature; 8) a drawing and annotation feature; 9) a hardware placement feature; 10) an eraser feature; 11) a 3D comparison feature, or 12) a co-registration feature. Each interaction feature is described below.

The spatial tracking feature may allow high precision tracking of the data in the Application State module 304. For any tracking subject, which is typically associated with the AR/VR/MR devices such as the hand controllers 16, 18 or the AR/VR/MR headset 20, the distance to any tracked object can be calculated to help the plurality of View Controllers 320 execute the interaction features and specify the one or more elements in the virtual scene being interacted by the user 2. Events can be associated to each tracked object, and they can be automatically triggered if the distance to the tracking subjects meets the predefined criteria.

When a tracking request is made, the distance can be interpreted by plurality of mechanisms, including but not limited to a signed distance function (SDF), a global SDF, or a closest point searching. The SDF is a mathematical function which defines a geometric primitive, or a union of multiple primitives and calculates the distance to it from any given point in a 3D space. It may define or approximate the tracking distance to any virtual scene element based on its transform data maintained by the transform and scene graph system 314. The sign of the distance value may describe whether the tracking subject is inside or outside of the tracked objects. For any volume layer of a volume data, the global SDF can be computed to aid in accurate tracking. The nearest position on the volume layer is estimated using the gradient of the SDF as a direction to project that distance. If the tracking request occurs for the subject outside the volume grid, the nearest point on the boundary of the volume grid is used to locate the nearest position on the surface. For any objects that can be represented or approximated by a collection of points, such as the polygon meshes with dense vertices, the tracking distance can be determined by searching the point closest to the tracking subject and calculating the distance to such point.

In accordance with the disclosed principles, the user maneuver feature may allow the user 2 to intuitively move, rotate, or scale one or more elements in the virtual scene in lifelike ways. This feature may allow the user 2 to observe the one or more 3D geometries such as the volume layers from the outside or from inside out. Using triggers or buttons on the hand controllers 16, 18 as well as the position and the orientation of the hands obtained from the AR/VR/MR interface 324, the corresponding View Controller 320 may generate commands to modify the translation, orientation and/or scale factor data maintained by the transform and scene graph system 314 to update the transform of one or more objects being maneuvered.

In one or more desired embodiments, when user 2 grabs with one hand by squeezing a trigger on the hand controller 16 or 18, one or more objects being maneuvered may be freely moved and rotated; when user 2 uses both hands to grab at empty space outside the objects, the objects may rotate and scale around their own geometric centers; when both hands grab inside an object, said object may be pivoted to user's both hands, and moved, rotated, and/or scaled with regards to the hand movement.

In one or more desired embodiments, the degree of freedom (DOF) of the maneuver may be constrained so the translation along one or more axes, and/or the rotation around one or more axes may be restricted to a limited range of motion, or even completely disabled. The user 2 may also define the rotational pivot. A set of gizmos may be present with the virtual scene elements to aid such maneuver with constrained DOF.

In accordance with the disclosed principles, the volume editing feature may allow the user 2 to modify one or more editable volume objects in real-time. The volume editing feature may implement a volume cutting tool, which allows the user 2 to cut the one or more editable volume objects and the surface representations associated therewith in user defined regions. When the user 2 confirms the cuts, the editable volume objects are then modified so the corresponding surface representation matches the cuts, and the additional volume objects may be generated to represent the newly cut partitions. The volume editing feature may also implement a paint-to-segment tool which allows the user 2 to define cut regions by gradually painting on the one or more volume objects by a virtual paint brush of various shapes and dimensions. The volume editing feature may also implement a volume sculpting tool which allows the user 2 to frequently modify the one or more volume objects and the surface representation associated therewith in the region specified by the user 2, to gradually remove materials from the represented geometry or add materials to it.

The measurement feature may provide accurate 3D and 2D measurements of a plurality of spatial properties based on the source dataset. An application system for the measurement feature may be implemented within the Application State module 304 to maintain and control the data that describes all measurement elements. The measurements may be one of more of the following: 1) the distance between two points, 2) the cumulative length of a polygonal chain, 3) the angle between two lines, 4) the angle between two planes, 5) the circumference of a circle, 6) the volumetric size of a user defined space, and/or 7) the volumetric size within an iso-surface. The measurements feature may further utilize a surface binding process to attach measurement points onto a surface of any volume layer or other 3D geometry close by, or onto a plane that display 2D images or renderings. As can be appreciated, this may increase the accuracy of the point placement, thus increasing measurement accuracy. When the user 2 maneuvers scene elements, the attached measurement points may be moved altogether, and the measurement results may be updated in real-time.

The snapshots feature may allow the user 2 to capture one or more pictures or videos of the virtual scene from any user specified perspective at any user defined time. One embodiment may allow the snapshot pictures to be saved as "PNG" files, and the snapshot videos to be saved as "MP4" files. The user 2 may look through a virtual viewfinder to help focus on the virtual objects to be captured. Once a snapshot is taken, a preview may be displayed on the virtual GUI 326, and the image may be saved under a designated path. The user 2 may switch between portrait and landscape modes as desired. Once the snapshots are saved, they may be reviewed by the user 2 on the virtual GUI 326, and the saved files may be accessed by the user 2 later.

The 3D visualization feature may provide real-time configurations of the visual properties of one or more 3D objects, which may be volume datasets or 3D geometries. These visual properties include but not limited to colors, level of transparency, iso-values, transfer functions, special visual effects achieved by shaders, etc. An application system may be implemented within the Application State module 304 to maintain, and control said visual properties. A graphics rendering module 322 may update the rendering of the one or more 3D objects in real-time to reflect the changes of the visual configuration.

The 2D visualization and overlay feature may present a 2D visualization of one or more 3D volume datasets or 2D image datasets in the virtual scene. A plurality of 2D rendering techniques, such as the multi-planar reconstruction (MPR) techniques, or the intensity projection techniques may be applied to visualize one or more volume datasets in 2D. In a desired embodiment wherein one or more 2D image datasets exist, the rendering of 2D dataset may also be presented. The rendering of multiple datasets may also be combined by an image fusion technique. The 2D visualization may be presented on a virtual GUI 326, a 2D GUI 328, or one or more 2D planes across the 3D visualization of the one or more volume datasets in the virtual scene. The planes may be the axial, sagittal, or coronal planes of the 3D volume, or they may be in any arbitrary orientation. Optionally, the 3D visualization of the volume datasets on either side of any plane may be culled out to better present both the internal structure of the volume datasets and the 2D rendering overlaid on the planes. The graphics rendering module 322 may update both the 3D visualization and the 2D rendering overlay in real-time based on the user interaction. A specific application system may be implemented within the Application State module 304 to maintain the data essential to the 2D visualization and overlay feature.

The drawing and annotation feature may allow the user 2 to draw or mark annotations in the virtual scene. One or more annotations, which may be points, lines, curves, symbols and/or texts may be created via a drawing and annotation tool controlled by the hand controller 16, 18. An application system for drawing and annotation may be implemented within the Application State module 304 to maintain and control said annotations. In a desired embodiment, the annotations may be applied on the surface of one or more 3D geometries such as volume layers or 3D geometries and moved along with the associated 3D objects. In a desired embodiment wherein one or more 2D rendering planes exist, the drawing and annotations may be applied on the 2D planes. The drawing feature may also include an option to measure the accumulated length of the lines or curves. Visual properties such as the color, the line width and the dash style may be configurable through the virtual GUI 326.

In a desired embodiment, a dynamic annotation, which may behave like a laser pointer, may be created, and controlled by the user 2 to point out specific positions and features on the one or more virtual scene elements for the benefit of the viewing audience. The point where the laser encounters the one or more surfaces or volume layers may be calculated by a ray casting technique, and the point may be visually highlighted to help draw attention to the point of interest. In a desired embodiment wherein, multiple users participate in a real-time interactive session via networking, the movement of the dynamic annotations may be synchronized with all users over the network through commands exchanged via the networking module 310.

The hardware placement feature may introduce one or more of the 3D models to the Application State module 304. These 3D objects can be independently included in the virtual scene or mounted to an existing element in the scene. In a desired embodiment wherein, the application is implemented for one or more of surgical planning, patient engagement and/or medical education, the hardware objects may be models of medical implants, surgical plates, screws, or surgical instruments. An application system for hardware placement may be implemented within the Application State module 304 to maintain and control the hardware models. In the transform and scene graph system 314 the hardware may be attached to any element in the scene.

In a desired embodiment wherein one or more 2D rendering planes exist, one or more projected contours or cross sections of one or more hardware models may be generated and superimposed on the 2D renderings of the volume or image datasets on the planes. The projected contours or cross sections may reflect the real-time position and orientation of the hardware models with respect to the 3D volumes or 2D images visualized on the corresponding 2D rendering planes. When the user 2 maneuvers one or more hardware models in the 3D space, the projected contours or the cross sections may be updated simultaneously. When the user 2 maneuvers one or more projected contours or the cross sections on 2D planes, the same movement may be applied to corresponding hardware models in real-time.

In a desired embodiment, the hardware models such as surgical plates may be bent against the surface of one or more volume layers, fitting the curvature of the anatomy structure. In another desired embodiment wherein the hardware models overlap with other 3D objects, the level of overlapping may be measured, and may be visualized by a color gradient on the surface of the objects representing the depth of intersection.

The eraser feature may allow the user 2 to erase one of more elements from the virtual scene. The eraser may be controlled by user's hand movement via the AR/VR/MR interface 324, and the tracking feature may monitor its distance to all erasable objects in the virtual scene. When the user 2 moves the eraser onto one or more erasable objects, a specific View Controller 320 of the eraser feature may issue a command to destroy the system data corresponding to said objects, which then triggers the removal of the objects from the view.

The 3D comparison feature may allow the user 2 to view and compare one or multiple sets of 3D objects. In one embodiment, the visualization of multiple sets of volume datasets, which may be the digital twins of the patient anatomy at different surgical phases, may be placed side by side for direct comparison. In another embodiment, the visualization of multiple volume dataset may overlay with each other for better comparisons. In another embodiment, the one or more volume objects may superimpose with their own mirrored inversion, highlighting the symmetric differences.

The co-registration feature may aid in aligning (co-registering) multiple elements, such as 3D volume datasets, 2D image datasets, and 3D geometries. The datasets may be of different modalities. The co-registration represents pairwise proper rigid transforms between the coordinate spaces of the elements. The 3D volumes may be visualized by either 2D multi-planar reconstruction (MPR) on axial/sagittal/coronal planes or overlaid maximum intensity projections (MIP). The co-registration may be performed manually via the mouse and keyboard controls, or semi-automatically via a partial Procrustes superimposition of plurality sets of user designated feature points with each set specifying the same feature on different elements. A resulting transformation matrix may be computed to describe the co-registration and said transformation matrix may be applied in the transform and scene graph system 314 to align these elements in the virtual scene.

In an example, the user 2, who may be a doctor, may want to view the 3D reconstructions of the head of a patient and conduct surgical planning using the workstation 10, 110. The doctor may use the workstation 10, 110 and may be wearing the AR headset 20 for viewing the 3D and 2D visualizations of the medical scans of the brain. The doctor may import the 3D medical scans as the cranial CT or MRI, the 2D medical scans such as DR, the segmentation of the medical scans and/or 3D geometries representing patient anatomy into the Application State module 304 via the input data source 322. The entirety of the Application State module 304 may also be previously saved in one or more files, which may be loaded on the workstation 10, 110 and viewed using the AR/VR/MR headset 20.

The AR/VR/MR interface 324 may update the doctor's hand position, the doctor's head position and orientation data from the AR/VR/MR hardware (i.e., the AR/VR/MR headset 20 and the hand controllers 16, 18) to the virtual GUI 326 or the plurality of View Controllers 320. The plurality of View Controllers 320 may issue one or more commands for creating, modifying, or destroying the data to the State Change Router 312. In turn, the State Change Router 312 may further route the commands to the Application State module 304, the undo/redo module 308 and/or the networking module 310. When said commands are received by the Application State module 304, the system data corresponding to one or more application systems may be created, modified, or destroyed; when said commands are received by the undo/redo module 308, they may be maintained in the undo/redo stack for future undo/redo operations, which may reverse previously executed commands; when said commands are received by the networking module 310, the commands may be sent to and synchronized with other users on the network. Through the execution of commands, the doctor may interact with the virtual representation of the patient head and use all available features in the application to explore the patient anatomy, conduct the surgical planning, perform the patient consultation, or assist the surgery.

The graphics rendering module 322 may render the 3D and 2D scans of the head anatomy in 3D space or on one or more 2D planes via the plurality of graphics rendering mechanisms. The graphics rendering module 322 may properly render both left and right views according to the position and orientation of the doctor's eyes. The images of the brain may be presented on the display screen 12 and the AR/VR/MR headset 20.

When AR superimposition is configured, the AR/VR/MR headset 20 may augment the user's view of patient anatomical structures, such as the patient head in this example, with visualizations of the corresponding digital representations. On the headset display, original images and virtual models may be superimposed onto the actual anatomical structures of the patient to reveal internal anatomy that is not externally visible. Additionally, surgical planning results may be overlaid onto the patient to assist in guiding surgical procedures. The virtual models and scans are configured to dynamically update their position and orientation to maintain accurate alignment when the corresponding anatomical structures are viewed from different angles or positions.

FIG. 5 illustrates components of a computing device 400 that may be utilized in or with the workstations 10, 110, 210 to execute or that may embody components of the disclosed embodiments. For example, the computing device 400 may include a memory 410, program instructions 412, one or more processors (e.g., processor and a graphics processor) 420 to execute the program instructions 412, one or more interfaces 430 (e.g., AR/VR/MR interface 324) connected via one or more buses 440. The memory 410 may be or include one or more of cache, RAM, ROM, SRAM, DRAM, RDRAM, EEPROM and other types of volatile or non-volatile memory capable of storing data. The one or more processors 420 may be or include multiple processors, a single threaded processor, a multi-threaded processor, a multi-core processor, or other type of processor capable of processing data.

The processors 420 may be operable to configure one or more modules, such as those mentioned above, to implement the methods and the underlying concepts disclosed herein. For example, a module may be implemented as a hardware circuit comprising custom very large-scale integration (VLSI) circuits or gate arrays, off-the-shelf semiconductors such as logic chips, transistors, or other discrete components. In another example, a module may be implemented in programmable hardware devices such as field programmable gate arrays, programmable array logic, programmable logic devices, graphics processing units, or the like. In some examples, a module may also be at least partially implemented in software for execution by various types of processors. An identified unit of executable code may, for instance, include one or more physical or logical blocks of computer instructions that may, for instance, be organized as an object, procedure, or function. Examples may include the executables of an identified module need not be physically located together or disparate instructions stored in different locations that, when joined logically together, comprise the module and achieve the stated purpose for the module. Further, the modules may be stored on a computer-readable medium, which may be, for instance, a hard disk drive, flash device, RAM, tape, and/or any other such non-transitory computer-readable medium used to store data without deviating from the scope of the subject matter disclosed herein. In a further example, a module of executable code could be a single instruction, or multiple instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network. It should be noted that one or more components of the computing device 400 may be located remotely and accessed via network. Accordingly, the system configuration provided in FIG. 5 is provided to illustrate how embodiments may be configured and implemented.

FIG. 6 illustrates schematic representations of the network environments implementing exemplary systems for rendering an operative guidance overlay in association with a patient, within the user's field of view, in accordance with an embodiment of the disclosure. As illustrated, the system 500 may include the computing device 502 in communication with one or more remote devices, such as one or more wearable augmented reality interface devices 506 and a set of sensors 504 over a network 508. In an example, the computing device 502 may be similar to the computing device 400 described in FIG. 5.

In an embodiment, the wearable augmented reality interface device 506 is implemented as an AR/VR/MR headset 20 configured to present computer-generated surgical guidance content in real time within the user's field of view. In one example, the wearable augmented reality interface device 506 includes a binocular micro display subsystem optically coupled to a waveguide or optical combiner assembly, such that stereoscopic virtual frames are projected simultaneously into the left eye and/or right eye of the user. Each frame may contain rendered virtual content including, but not limited to, segmented anatomical models, predicted incision vectors, virtual implant templates, and contextual annotations, all registered to the underlying physical anatomy of the patient.

In an exemplary embodiment, the wearable augmented reality interface device 506 includes display-integrated subsystems for multimodal interaction and user feedback. In one implementation, the wearable augmented reality interface device 506 includes one or more embedded eye-tracking sensors, positioned adjacent to the optical waveguide or display module. These sensors are configured to detect the user's gaze vector and fixation patterns, enabling gaze-based control of virtual elements. For example, gaze may be used to trigger user interface responses such as annotation toggling, element highlighting, or menu activation.

In some embodiments, the wearable augmented reality interface device 506 further includes an integrated microphone array, which enables hands-free voice interaction. The microphone array is operable to receive voice input for command execution tasks such as activating overlays, switching between anatomical layers, or initiating registration routines.

In another embodiment, audio feedback may be provided through a bone-conduction speaker system or alternative acoustic transducers (e.g., in-ear drivers). The audio system may be configured to deliver contextual signals to the user, including alignment confirmation tones, procedural prompts, overlay status indicators, or verbal system messages, while maintaining ambient awareness critical to operating room environments. In an embodiment, the wearable augmented reality interface device 506 is communicatively linked to the computing device 502 via a low-latency, high-throughput communication interface. This interface may include, but is not limited to, wired protocols such as USB, HDMI, or DisplayPort, or wireless communication links such as cellular network, Wi-Fi, or Bluetooth. The interface supports hardware-accelerated transmission of video streams and bidirectional sensor telemetry, including time-synchronized pose and interaction data.

In a preferred embodiment, the communication architecture ensures sub-millisecond jitter and maintains continuous spatial coherence between the rendered virtual content and the patient's physical anatomy, even under dynamic motion conditions. The wearable augmented reality interface device 506 thereby enables high-fidelity surgical visualization with predictive alignment stability across all phases of the operative workflow.

In an embodiment, the set of sensors 504 is operatively arranged in association with the wearable augmented reality interface device 506 and is configured to capture multimodal data relevant to both the user and the patient during an operative procedure. The set of sensors 504 may include a combination of vision-based, inertial, and optionally physiological sensors, enabling comprehensive tracking and environmental awareness required for precise spatial registration and overlay rendering.

In certain embodiments, the set of sensors 504 includes at least one pair of RGB cameras mounted on the outward-facing surface of the wearable augmented reality interface device 506, configured to capture real-time stereoscopic imagery of the surgical field. In an example, the cameras are calibrated to detect passive visual markers or active light-emitting optical markers, which may be affixed to the patient, operative instruments, or surrounding fixtures. The captured imagery is streamed to the computing device 502, where image-based registration algorithms are employed to spatially align the virtual anatomical model with the physical patient anatomy based on detected marker positions. In an embodiment, the set of sensors 504 further includes an infrared (IR) depth sensor (e.g., a time-of-flight camera or structured light sensor), co-located with the RGB cameras, which provides three-dimensional surface mapping of the patient's body. This supports continuous registration by capturing patient movement or respiratory motion in real time, and enhances the fidelity of the rendered guidance overlay.

In further embodiments, in addition to vision-based tracking, the set of sensors 504 integrates the six-degree-of-freedom (6-DoF) inertial measurement unit (IMU), including one or more accelerometers, gyroscopes, and optionally magnetometers. The IMU is configured to output high-frequency orientation and translational motion data of the wearable augmented reality interface device 506, which is fused with other sensor inputs to determine the pose of the user relative to the patient.

In operation, the computing device 502 is configured to receive image data associated with the patient. The image data indicates an anatomical structure of the patient and a structure of each of the one or more operative instruments. In an exemplary embodiment, the image data may include volumetric medical imaging acquired using diagnostic modalities such as computed tomography (CT) or magnetic resonance imaging (MRI). The image data may include the captured anatomical regions relevant to the intended surgical procedure, including but not limited to skin, skeletal components, muscles, lungs, or pathological areas such as pneumothorax or hemothorax.

In one example, the received image data is formatted in DICOM, STL, or other medical imaging standards and may be converted into NIfTI volumetric format using preprocessing pipelines. These conversions may leverage libraries such as SimpleITK or custom scripts developed in medical imaging environments (e.g., 3D Slicer). The conversion standardizes the dataset and prepares it for subsequent segmentation and modeling tasks.

In an embodiment, the image data may also include patient-specific annotations, radiographic markers, or prior surgical hardware visible in the imaging volume. The image data serves as the foundational input for constructing virtual anatomical representations and supporting surgical planning tasks and is ingested by the computing device 502 through a local or networked data interface. In addition to the anatomical information, the image data may further include representations of the structure of each of the one or more operative instruments intended for use during the procedure. Such instrument-related data may be obtained from preoperative scans capturing the instruments in situ, from manufacturer-provided 3D CAD models, or from intraoperative imaging systems capable of visualizing instrument geometry. Including the structure of each operative instrument within the same dataset enables the computing device 502 to accurately model both the patient anatomy and the instruments in a unified spatial reference frame, which in turn supports more precise registration, tracking, and real-time guidance overlay generation.

Further, the computing device 502 is configured to generate one or more virtual models based on the image data. The one or more virtual models includes at least one of: a virtual anatomical model of the anatomical structure of the patient, or one or more virtual instrument models associated with the one or more operative instruments. In an example, the computing device 502 processes volumetric medical imaging data, such as, but not limited to, computed tomography (CT) or magnetic resonance imaging (MRI) scans, to produce a three-dimensional representation of patient-specific anatomy suitable for visualization and interaction within an augmented reality environment.

In one example, the computing device 502 applies a segmentation pipeline to delineate anatomical regions from the image data. This may include the use of automated segmentation algorithms based on convolutional neural networks (CNNs), including architectures such as U-Net, nnU-Net, or Swin UNetR. These models are trained to identify and isolate structures of clinical interest, such as bones, soft tissue, lung parenchyma, or pathologies, within the volumetric image. Similarly, virtual instrument models may be generated from preoperative scans, manufacturer-supplied CAD files, or intraoperative captures depicting the geometry of each operative instrument so that both the anatomy and the instruments are represented within the same spatial reference frame. The resulting segmented output is converted into a 3D surface mesh or volumetric label map, which is used to construct the virtual anatomical model. In some embodiments, the AI model includes a multi-layered structure, with each layer corresponding to a specific anatomical component, such as, but not limited to, skin, ribs, intercostal muscles, or pathological volumes allowing for independent adjustment of visual properties including transparency, color gradient, and spatial orientation.

In one illustrative example, the system may generate a thoracic model from CT data that includes fractured ribs, the lung boundary, regions of pneumothorax, and overlying skin together with virtual representations of one or more operative instruments registered in the same coordinate system. These structures and instruments are presented in a patient-specific three-dimensional configuration, enabling the AI model to serve as a digital twin of the operative field for downstream planning and intraoperative visualization.

Further, the computing device 502 is configured to receive the sensor data associated with at least one of: the user, the one or more operative instruments, or the patient. In an embodiment, the sensor data is transmitted from the set of sensors 504, which are operatively associated with the wearable augmented reality interface device 506. The sensor data includes time-synchronized positional, visual, and interaction-related measurements relevant to maintaining spatial registration and alignment between the virtual anatomical model, the virtual instrument models, and the corresponding physical patient anatomy and operative instruments. In an exemplary embodiment, the computing device 502 receives this sensor data through a communication interface that supports high-throughput and low-latency data transmission. The received sensor data includes values representing the spatial pose of the user, orientation changes, and marker positions associated with patient anatomy, operative instruments, or surgical reference objects. The sensor data is used to maintain accurate spatial tracking, support predictive pose adjustments, and respond to dynamic user movements or changes in the patient's position or movement of operative instruments during the surgical procedure. In some embodiments, the sensor data further includes information indicative of user interaction events, such as detected gestures, voice commands, or gaze-based input signals. Upon reception, the computing device 502 interprets the sensor data points to update the operative guidance logic and control the behavior of the augmented reality display system accordingly.

Further, the computing device 502 is configured to dynamically generate guidance overlay data associated with at least one of: the anatomical structure of the patient, or the one or more operative instruments, based on the one or more virtual models and the sensor data. The guidance overlay data indicates the operative guidance overlay including one or more guidance markers associated with the patient, the one or more operative instruments, or both. The guidance overlay data includes spatially registered visual indicators that are rendered in association with the physical patient anatomy and, where applicable, the corresponding operative instruments during an operative procedure. In an embodiment, the guidance overlay data includes one or more guidance markers, which are digitally rendered annotations, visual landmarks, or directional vectors associated with the anatomical structures identified in the virtual anatomical model or with features of the virtual instrument models. The one or more guidance markers are generated by the computing device 502 in alignment with clinical objectives such as surgical incision planning, implant positioning, identification of pathological regions, or optimal instrument trajectories and approach angles. The guidance markers may be anchored to anatomical landmarks or instrument reference points derived from segmented volumetric imaging data and dynamically updated in response to changes in user pose, patient movement, or instrument manipulation.

In an example, the computing device 502 generates a linear vector extending from a rib fracture site to the external skin surface, oriented normal to the bone plane, to indicate an optimal incision path, or generates a dynamic trajectory marker aligned with a surgical instrument tip to guide its approach toward the target anatomy. In another example, a visual bounding volume or highlight contour may be rendered around a region of pneumothorax or hemothorax to guide surgical access or drainage, or a virtual safety zone may be displayed around a sensitive structure to warn when an instrument enters the area. The guidance overlay data is generated in real time, allowing for continuous updates in response to incoming sensor data, such as head orientation changes, patient motion, or movement of the operative instruments and gesture-based user interaction. In certain embodiments, the computing device 502 modulates the visual appearance of the guidance markers, such as, but not limited to, color, transparency, or flashing behavior based on confidence levels or alignment accuracy metrics derived from tracking and registration algorithms. By generating the guidance overlay data in a dynamic and context-aware manner, the computing device 502 ensures that the virtual anatomical content and instrument-related information remain clinically relevant, spatially accurate, and responsive to the procedural workflow during all phases of the surgical intervention.

Further, the computing device 502 is further configured to render, using the wearable augmented reality interface device 506, the operative guidance overlay in association with the patient based on the guidance overlay data. The rendering of the operative guidance overlay includes continuous alignment of the virtual anatomical model with the patient and continuous alignment of the one or more virtual instrument models with the corresponding operative instruments. The rendering operation may include projecting the guidance overlay content, including anatomical models, virtual instrument models, surgical annotations, and visual guidance markers, into the user's field of view such that it is spatially aligned with the corresponding regions of the patient's body and the operative instruments being tracked. In an embodiment, the operative guidance overlay includes multiple visual elements that are dynamically composited within the augmented reality display, including semi-transparent anatomical structures, color-coded incision lines, implant templates, virtual representations of instruments, and interactive indicators rendered in three-dimensional space relative to the physical anatomy of the patient and the physical position of the operative instruments, as established through prior model-to-patient/instrument registration and ongoing sensor feedback.

The rendering of the operative guidance overlay includes continuous alignment of the virtual anatomical model with the physical patient and continuous alignment of the virtual instrument models with the physical operative instruments. This is achieved by continuously updating the rendered pose of the overlay content in response to real-time sensor data received from the set of sensors 504. The alignment process accounts for changes in the user's head orientation, patient movement, or intraoperative repositioning and for movement or repositioning of the operative instruments by adjusting the virtual content accordingly to preserve spatial coherence.

In one example, as the surgeon shifts position during the procedure, the computing device 502 receives updated head pose data and reprojects the guidance overlay to match the surgeon's updated viewpoint, thereby maintaining visual lock between the displayed virtual anatomy, the virtual instrument models, and the actual surgical site. In another example, real-time tracking of spatial reference markers 36 ensures that the guidance overlay remains anatomically and instrumentally accurate even if the patient or the operative instruments undergo subtle physical adjustments on the operating table. The rendering operation ensures that the virtual content remains stable, visually intuitive, and clinically useful throughout the duration of the surgical procedure.

FIG. 7 is a flowchart 600 that illustrates an exemplary method for spatially aligning the virtual anatomical model with the anatomical structure of the patient, in accordance with an embodiment of the disclosure. FIG. 7 is explained in conjunction with elements from FIGS. 1, 2, 3, 4, 5, and 6. With reference to FIG. 7, there is shown the flowchart 600. The operations of the exemplary method may be executed by any computing system, for example, by the system 500 of FIG. 6, the computing device 502 of FIG. 6, or the processor 502A of FIG. 6. The operations of the flowchart 600 may start at 602.

At 602, one or more spatial reference markers 36 relating to the patient, the one or more operative instruments, or both are identified and localized. In an embodiment, the computing device 400 is configured to identify and localize the one or more spatial reference markers 36, wherein the markers comprise at least one of: a passive visual marker, a light-emitting optical marker, an electromagnetic marker, or any combination thereof. In another embodiment, the computing device 502 or the processor 502A decodes the detected markers to determine their spatial positions and orientations within the operative field.

In one embodiment, the passive visual markers include visually encoded identifiers that are detectable using computer-vision techniques, such as Quick Response (QR) codes, AprilTags, ArUco markers, or passive reflective spheres. The light-emitting optical markers may include active diodes or beacons emitting visible or infrared light. The electromagnetic markers may include coils or transponders detectable by electromagnetic tracking systems. These markers can be affixed to the patient, integrated into surgical drapes, attached to handheld instruments, or mounted on rigid fixtures secured to the patient or the instrument body. The set of sensors 504 captures the signals or images of one or more markers, and the computing device 502 computes the position, orientation, and identifier of each marker within the detection field.

In one illustrative example, an AprilTag functioning as a passive visual marker is affixed to a rigid arm secured to the patient's thorax, while an infrared LED cluster functioning as a light-emitting marker is attached to a surgical instrument. The system detects both marker types through stereo cameras and optical sensors, and computes their poses in three-dimensional space. These detected poses are then used as fixed anchor points for aligning the segmented ribcage model and the corresponding virtual instrument model within the augmented reality environment.

At 604, at least one of the following is performed based on the sensor data: (i) the virtual anatomical model is registered to and spatially aligned with the anatomical structure of the patient, or (ii) one or more virtual instrument models are registered to and spatially aligned with their corresponding physical operative instruments. In an embodiment, the computing device 502 or the processor 502A is configured to perform this spatial alignment by combining real-time sensor data, such as position and orientation streams from the set of sensors 504, with the detected locations of the markers. This alignment process ensures that the virtual anatomical content and the virtual instrument representations are accurately registered to their physical counterparts throughout the procedure.

In one embodiment, the computing device 502 applies a registration algorithm that fuses pose estimates derived from inertial or tracking sensors with the known spatial relationships of the spatial reference markers 36 affixed to the patient or attached to the surgical instruments. The resulting transformation matrix is used to adjust the position and orientation of the virtual models in three-dimensional space so that they remain visually coherent with the underlying anatomy and instrument tips in the augmented reality display.

In one illustrative example, an AprilTag functioning as a passive visual marker is secured to the patient's thorax, while an infrared LED cluster functioning as a light-emitting optical marker is attached to a surgical instrument. The system detects both markers through the stereo cameras and computes their poses in three-dimensional space. Using these detected poses and the streaming sensor data, the computing device 502 spatially aligns the segmented ribcage model with the patient's actual thorax and simultaneously aligns the virtual instrument model with the physical surgical tool. This allows the operative guidance overlay to remain precisely anchored to both the patient anatomy and the instrument trajectory even as the user or patient moves during the procedure.

In an embodiment, the sensor data includes at least one of: environment data, user interaction data associated with the user, orientation data associated with the user, pose data associated with the patient, or alignment data associated with the one or more markers. The environment data provides context regarding the operating room space, lighting, and surrounding structures, which may be used to filter out occluded regions or improve the robustness of tracking. The user interaction data includes input derived from gestures, eye gaze, or voice commands, which may be used to initiate manual fine-tuning of model alignment. The orientation data associated with the user refers to the rotational movement of the user's head, captured by inertial sensors, and is used to ensure the AI model appears consistently registered from any viewing angle. The pose data associated with the patient reflects the dynamic position and orientation of the patient on the operating table and is used to update the model alignment if the patient moves. Finally, the alignment data associated with the one or more markers includes spatial coordinates and identity tags of external or anatomical markers, allowing the system 500 to maintain real-time consistency between the virtual and physical anatomical frames.

In another embodiment, the user interaction data associated with the user includes at least one of: one or more gestures, one or more voice commands, and one or more eye movements. This data is captured by one or more components of the system 500 and transmitted to the computing device 502 for interpretation and integration into the operative workflow. The user interaction data serves as a control mechanism for enabling hands-free and intuitive manipulation of the virtual anatomical model and associated guidance overlays within the augmented reality environment. In one embodiment, gesture input is detected through hand-tracking sensors, external vision systems, or AR hand controllers associated with the wearable augmented reality interface device 506. Recognized gestures may include directional swipes, pinches, rotations, or point-and-select motions that allow the user to reposition virtual content, toggle anatomical layers, or activate planning modules.

In another embodiment, voice commands are received through a microphone array integrated within the wearable augmented reality interface device 506. The microphone system is configured to support voice recognition of predefined command phrases that correspond to user actions such as initiating registration routines, switching between virtual display modes, confirming alignment status, or recording procedural landmarks. In an additional embodiment, eye movement data is captured by embedded eye-tracking sensors positioned near the optical path of the wearable augmented reality interface device 506. This data includes the user's gaze vector, fixation points, and blink patterns. The computing device 502 uses this information to enable gaze-based interaction with the augmented reality interface, including highlighting anatomical structures, selecting guidance markers, or confirming user attention during critical procedural steps.

In one example, the user may fixate their gaze on a specific virtual implant, then perform a voice command to anchor the implant at that location. In another example, a leftward hand swipe may be used to remove a soft tissue layer from the view, while a rightward swipe restores it. The inclusion of multimodal interaction gesture, voice, and gaze supports a highly intuitive and sterile-compatible control interface, reducing the need for physical contact with hardware and enhancing usability in operative environments.

At 606, periodically updated sensor data from the set of sensors is received. At 606, periodically updated sensor data from the set of sensors is received. In an embodiment, the computing device 502, or the processor 502A thereof, is configured to periodically receive updated sensor data from the set of sensors 504. This periodic reception occurs at a defined refresh rate, such as 60 Hz, 90 Hz, or 120 Hz, ensuring that the spatial tracking, alignment, and interaction logic remain current with the physical state of the user, the patient, and the operative instruments. The updated sensor data may include time-stamped orientation, position, velocity, or interaction events captured by inertial or tracking subsystems integrated into or associated with the wearable augmented reality interface device 506 and the spatial reference markers 36.

In one embodiment, the periodic reception of updated sensor data enables the computing device 502 to maintain low-latency synchronization between the virtual models and the real-world environment. Each incoming batch of data is immediately processed to update pose estimates, refresh alignment transforms, and adjust the rendering of the operative guidance overlay.

In one illustrative example, the computing device 502 receives updated head-pose data from the wearable augmented reality interface device 506 and simultaneous marker-tracking data from the cameras at 120 Hz. These periodic updates allow the processor 502A to anticipate the surgeon's next viewpoint and re-align the virtual anatomical model and virtual instrument models accordingly. As a result, even during rapid movements or changes in instrument position, the operative guidance overlay remains stable and accurately registered to both the patient's anatomy and the surgical tools.

At 608, the computing device 502, or the processor 502A thereof, is configured to continuously maintain the spatial alignment of at least one of the following, based on updated sensor data: (i) the virtual anatomical model with the patient's anatomical structure, or (ii) one or more virtual instrument models with their corresponding physical operative instruments. This dynamic alignment is sustained as the patient or the operative instruments move relative to the user's viewpoint, thereby compensating for such movement and preserving accurate spatial correspondence.

In one embodiment, the computing device 502 fuses pose updates derived from inertial and tracking sensors with the known positions of the spatial reference markers 36 attached to the patient and surgical tools. The resulting transformation matrices are applied frame-by-frame to update the spatial location and orientation of the virtual anatomical model and virtual instrument models in the augmented reality environment, ensuring that the overlay content remains visually coherent and clinically reliable.

In one illustrative example, as the surgeon shifts position around the operating table and simultaneously reorients a tracked surgical instrument, the computing device 502 receives continuous updates of head pose, patient markers, and instrument markers at 120 Hz. Using this data, the processor 502A dynamically recalculates alignment so that the segmented ribcage model stays anchored to the patient's thorax and the virtual instrument model stays precisely aligned with the physical instrument tip. This continuous alignment allows the operative guidance overlay to appear stable and correctly registered from every viewpoint, even under rapid motion or intraoperative adjustments.

FIG. 8 is a flowchart 700 that illustrates an exemplary method for generating the guidance overlay data associated with the anatomical structure of the patient, in accordance with an embodiment of the disclosure. FIG. 8 is explained in conjunction with elements from FIGS. 1, 2, 3, 4, 5, 6, and 7. With reference to FIG. 8, there is shown the flowchart 700. The operations of the exemplary method may be executed by any computing system, for example, by the system 500, the computing device 502, or the processor 502A of FIG. 6. The operations of the flowchart 700 may start at 702.

At 702, an algorithm is applied to at least one of the orientation data or the pose data. In an embodiment, the system 500 is configured to apply an algorithm to at least one of the orientation data or the pose data. In an embodiment, the computing device 502 or the processor 502A is configured to apply the algorithm to at least one of the orientation data or the pose data.

In an embodiment, the algorithm is a real-time predictive or compensatory processing routine configured to operate on incoming tracking data, including at least one of: orientation data associated with the user, or pose data associated with the patient. The algorithm is designed to generate latency-adjusted orientation data and/or pose data, which is used to dynamically stabilize the rendering of the operative guidance overlay in response to motion by the user or the patient. The algorithm may be implemented using time-series inference or estimation techniques such as a Kalman filter, a complementary filter, or an adaptive prediction model; in certain embodiments the algorithm may include a machine-learning-based predictor such as an LSTM, GRU, RNN, transformer, or a fused sensor model that integrates inertial and tracking data streams. The purpose of the algorithm is to infer near-future spatial orientation or pose values by observing the temporal evolution of prior motion inputs. The orientation data associated with the user includes a sequence of angular rotations, such as quaternion values or rotation matrices captured by the inertial measurement unit embedded in the wearable augmented reality interface device 506. The pose data associated with the patient includes time-stamped position and orientation estimates derived from marker tracking or vision-based surface reconstruction.

The computing device 502 applies the algorithm to this sequence of tracking data to generate a forward-predicted pose or orientation value, which is used to anticipate the future spatial configuration of the user's view or the patient's anatomy at a short time horizon that corresponds to the system's end-to-end rendering latency. In one embodiment, the computing device 502 receives orientation data from the wearable augmented reality interface device 506 and applies the algorithm to estimate where the user's head will be oriented approximately 10 to 25 milliseconds in the future. The latency-adjusted data is then used to reposition the virtual anatomical model within the user's view, thereby ensuring that the operative guidance overlay remains stable and spatially coherent, even during rapid or unexpected head movements.

In another embodiment, the pose data associated with a patient-mounted marker is used as input to the algorithm to produce a latency-adjusted prediction of the marker's future position. The overlay elements associated with that marker, such as a guidance vector or a procedural annotation, are repositioned based on the algorithm's output to ensure accurate and real-time alignment. The application of the algorithm to orientation or pose data enables the system 500 to generate guidance overlay data that is responsive to motion dynamics while compensating for processing and rendering delay, thereby improving the visual fidelity and clinical reliability of the augmented reality interface.

At 704, latency-adjusted orientation data associated with the user and latency-adjusted pose data associated with at least one of: the patient or the one or more operative instruments are determined. In an embodiment, the system 500 is configured to determine, based on application of the algorithm, latency-adjusted orientation data associated with the user and latency-adjusted pose data associated with at least one of: the patient or the one or more operative instruments. In an alternate embodiment, the computing device 502 or the processor 502A is configured to determine these latency-adjusted values by applying the algorithm to a sequence of real-time orientation and pose measurements received from the wearable augmented reality interface device 506 and the associated tracking sensors.

The latency-adjusted orientation and pose data represent forward-predicted estimates of the user's head orientation and the patient's or operative instruments' positions at a future time offset that corresponds to the cumulative delay in the system's data acquisition, processing, and display rendering pipeline. This offset accounts for latency introduced by inertial or tracking sensor sampling, wireless transmission to the computing device 502, computational processing of overlay content, and the refresh cycle of the augmented reality display.

In an embodiment, the orientation data includes quaternion or Euler angle values sampled at high frequency by the inertial measurement unit embedded within the wearable augmented reality interface device 506, while the pose data includes time-stamped position and orientation estimates derived from marker tracking or vision-based surface reconstruction of the patient or the operative instruments. These values are sequentially processed by the algorithm, which outputs predicted orientation and pose vectors aligned to a future timestamp, typically within a 10 to 25 millisecond window from the current sensor readings.

In one example, the computing device 502 receives orientation data at 120 Hz from the wearable augmented reality interface device 506 and pose data from sensors tracking the patient and operative instruments. A rolling buffer of recent values is passed to the algorithm, which outputs the anticipated orientation of the user's head and the anticipated pose of the patient or instrument at a 16-millisecond look-ahead point. These predicted values are stored as the latency-adjusted orientation and pose data and are used by downstream modules for virtual model positioning.

In another example, when the user performs a rapid rotational movement of the head—such as turning from the instrument tray back toward the patient—or when an operative instrument is moved toward a target region, the system 500 uses the latency-adjusted orientation and pose data to pre-emptively reposition the virtual anatomical content and virtual instrument models. This ensures that the rendered operative guidance overlay remains perceptually fixed to the correct anatomical region and instrument location without delay or visual lag.

At 706, guidance overlay data associated with the anatomical structure of the patient, the one or more operative instruments, or both is generated. The guidance overlay data is generated based on the latency-adjusted orientation data and the latency-adjusted pose data. In an embodiment, the system 500 is configured to generate the guidance overlay data associated with the anatomical structure of the patient, the one or more operative instruments, or both based on the latency-adjusted orientation data and the latency-adjusted pose data. In an alternate embodiment, the computing device 502 or the processor 502A is configured to generate the guidance overlay data by utilizing the predictive orientation and pose outputs generated from the algorithm to ensure real-time visual alignment between the rendered virtual content, the physical anatomy, and the physical operative instruments. The generation of guidance overlay data includes defining spatial positions, shapes, and visual properties of digital content such as anatomical highlights, incision paths, implant outlines, procedural annotations, instrument trajectories, and instrument-related safety zones that are contextually tied to regions of interest within the virtual anatomical model or the virtual instrument models.

The latency-adjusted orientation data and latency-adjusted pose data are used by the computing device 502 to determine the anticipated point of view of the user and the expected positions of the patient or operative instruments at the time the augmented reality content will be displayed. This ensures that the guidance overlay data is generated and rendered in alignment with where the user is expected to look and where the patient structures or instruments will be located, compensating for latency in the system's sensor capture and rendering pipeline.

In one example, if the latency-adjusted orientation data indicates that the user will be viewing the patient's lateral thorax at a forward time offset and the latency-adjusted pose data predicts the trajectory of an instrument approaching the site, the guidance overlay data generated by processor 502A will include anatomical boundaries for fractured ribs, overlaid surgical templates for plating, arrows indicating the recommended implant alignment, and a projected path indicator for the instrument's tip all precisely projected onto the anatomical site corresponding to the user's predicted field of view and the instrument's predicted position.

The guidance overlay data may also include dynamic visual parameters such as transparency, brightness, edge sharpness, or color highlighting based on clinical priorities, user preferences, or tracked motion metrics of both anatomy and instruments. The processor 502A continuously updates this overlay content in response to new latency-adjusted orientation and pose data to maintain a consistent and visually stable projection of the virtual anatomical model and the virtual instrument models within the field of view.

FIG. 9 is a flowchart 800 that illustrates an exemplary method for rendering the operative guidance overlay within the field of view of the user based on the second pose estimate, in accordance with an embodiment of the disclosure. FIG. 8 is explained in conjunction with elements from FIGS. 1, 2, 3, 4, 5, 6, 7, and 8. With reference to FIG. 9, there is shown the flowchart 800. The operations of the exemplary method may be executed by any computing system, for example, by the system 500, the computing device 502, or the processor 502A of FIG. 6. The operations of the flowchart 800 may start at 802.

At 802, an initial pose estimate of the operative guidance overlay is generated based on the sensor data. In an embodiment, the computing device 502 or the processor 502A is configured to generate the initial pose estimate of the operative guidance overlay based on the sensor data. The initial pose estimate defines the initial spatial configuration including position, orientation, and scale of the operative guidance overlay relative to the user's current viewpoint. This pose estimation process includes mapping the location of anatomical structures, patient-mounted markers, or environmental landmarks into a shared coordinate space and determining the appropriate alignment of the virtual content with respect to the sensor data acquired during the procedure.

In one embodiment, the sensor data includes positional and orientation data acquired from tracking markers, inertial measurement units, or depth-sensing modules. The computing device 502 fuses these inputs to compute a stable reference frame for the patient and then determines where and how the operative guidance overlay should appear in three-dimensional space from the user's perspective.

In one illustrative example, the user positions themselves above the patient's thoracic region. The computing device 502 receives head pose data from the wearable augmented reality interface device and surface data from a depth camera tracking the patient's chest contour. The processor 502A computes the initial pose estimate that positions the operative guidance overlay including segmented ribs, muscle tissue, and implant indicators, so that it appears fixed over the correct anatomical region in the user's projected field of view.

At 804, a pose at each new time step is predicted using a previous estimate and a dynamic model. In an embodiment, the computing device 502 or the processor 502A is configured to predict a pose at each new time step using a previous estimate and a dynamic model. The dynamic model operates as a real-time spatial prediction engine configured to improve the fidelity of virtual-to-physical correspondence by projecting the current pose estimate forward in time based on system dynamics and tracking inputs.

In some embodiments, the dynamic model functions as a predictive filtering mechanism that accounts for noise, drift, or incomplete tracking data and produces a forward-predicted overlay pose that remains stable under dynamic surgical conditions. In an alternate embodiment, the previous pose estimate, which includes an approximation of the overlay's position and orientation relative to the user, patient, and/or instruments, is input into the dynamic model along with live sensor measurements, such as head orientation data, patient pose data, depth map coordinates, or marker locations. The model computes a predicted pose for the next time step based on the temporal evolution of these parameters, enabling the system to maintain an accurate and responsive augmented reality experience.

In one example, the computing device 502 receives the initial pose of a rib overlay generated at operation 802 together with updated orientation data from the wearable augmented reality interface device and new depth measurements from the patient's thorax. The dynamic model predicts the overlay's pose at the next display frame, evaluating deviations between expected and observed marker positions and outputting a forward-projected transformation so that the overlay aligns precisely with the patient's anatomical region in the user's real-time view.

In another embodiment, if minor shifts in the user's viewpoint occur due to natural head movement, the dynamic model predicts the overlay pose for the next time step to maintain consistent spatial lock, thereby eliminating visual drift or lag. The predicted pose output by the model ensures that the guidance overlay remains perceptually anchored to the correct anatomical structure throughout the procedure. By predicting a pose at each new time step using the previous estimate and the dynamic model, the system 500 enhances the stability, precision, and responsiveness of the augmented reality guidance interface, enabling high-confidence intraoperative visualization and spatial navigation.

At 806, a new measurement from the sensor data is obtained at each new time step. In an embodiment, the computing device 502 or the processor 502A is configured to obtain updated sensor measurements at every refresh interval to complement the previously predicted pose. These new measurements may include, for example, updated head-orientation data from the wearable augmented reality inter-face device 506, patient pose data from spatial reference markers 36, or instrument-tracking coordinates from intra-operative sensors. Each newly obtained measurement pro-vides real-time information that is used to refine and update the operative guidance overlay.

In one embodiment, the computing device 502 obtains new measurements from the sensor data as a continuous input stream, performing repeated acquisitions at a defined refresh rate, such as 60 Hz or 120 Hz. The incoming measurements reflect the most current alignment of the virtual anatomical model and virtual instrument models relative to the physical patient, the operative instruments, and the user's perspective, and are captured in response to even minor shifts in spatial configuration.

In an illustrative example, the user is actively reposition-ing their viewpoint around the operative field. At each frame update the computing device 502 obtains a new set of sensor measurements to account for rotational movement detected in the user's orientation data and drift observed in marker tracking. The processor 502A uses this information together with the predicted pose to maintain the correct position and orientation of the virtual overlay within the user's field of view. In another example, subtle changes in the patient's posture or respiration are captured through newly obtained pose data, and the computing device 502 uses these updated measurements to ensure that the virtual overlay remains consistently aligned with the patient's anatomy.

At 808, the initial pose estimate is updated to determine an updated pose estimate by optimally blending the pre-dicted pose and the new measurement, accounting for their respective uncertainties. In an embodiment, the computing device 502 or the processor 502A is configured to update the initial pose estimate to determine an updated pose estimate by optimally blending the predicted pose and the new measurement, accounting for their respective uncertainties. The blending process weights the predicted pose and the newly obtained measurement according to their confidence levels or estimated error covariances, producing a single updated pose estimate that best reflects the true spatial configuration of the user, patient, and operative instruments at that time step. This updated pose estimate represents a refined and stabilized spatial alignment of the operative guidance overlay, enabling the system to maintain accurate registration of virtual anatomical and instrument models with their physical counterparts despite motion, sensor noise, or transient occlusions.

In one example, the computing device 502 predicts the pose of a virtual instrument model approaching a rib fracture site based on previous estimates and then receives a new measurement from spatial reference markers on the instru-ment shaft and the patient's skin surface. The processor 502A applies an optimal blending algorithm, such as a Kalman filter, to fuse the predicted pose and the new measurement, weighting each according to its estimated uncertainty. The resulting updated pose estimate corrects for any drift in the prediction and compensates for minor tracking errors, ensuring that the instrument's virtual trajec-tory and the patient's anatomical model remain precisely aligned within the user's augmented reality view. In another example, when the user makes a rapid head movement, the updated pose estimate allows the operative guidance overlay to remain visually locked to the correct anatomical region and instrument tip without perceptible lag orjitter.

At 810, the operative guidance overlay is rendered within the field of view of the user based on the updated pose estimate. In an embodiment, the computing device 502 or the processor 502A is configured to render the operative guidance overlay within the field of view of the user based on the updated pose estimate, such that the operative guid-ance overlay appears spatially stable with respect to the anatomical structure of the patient, the one or more operative instruments, or both.

The rendering operation utilizes the updated pose estimate as the definitive spatial reference for positioning the virtual anatomical model, virtual instrument models, and associated guidance markers relative to the user's current viewpoint and the real-world surgical field. The rendered content includes three-dimensional overlays such as segmented ana-tomical volumes, virtual representations of operative instru-ments, incision vectors, implant templates, procedural anno-tations, and other clinically relevant indicators derived from preoperative imaging and planning workflows.

In an embodiment, the operative guidance overlay is projected into the user's field of view via the wearable augmented reality interface device 506, using binocular display optics that ensure stereoscopic depth and spatial coherence. The computing device 502 renders the virtual content with real-time adjustments based on the updated pose estimate, thereby compensating for any movement of the user, patient, or operative instruments.

In one illustrative example, the system renders a translu-cent lung overlay, rib fracture annotations, implant trajectory vectors, and a virtual instrument path precisely aligned with the patient's thoracic region and the approaching surgical tool. As the user shifts position or the instrument moves, the updated pose estimate is applied by the processor 502A, and the overlay remains visually fixed to the same anatomical location and instrument tip without drift or delay.

In another embodiment, spatial transitions between over-lay states—such as toggling anatomical layers, rotating a virtual implant, or changing instrument trajectories—are executed in reference to the updated pose estimate to main-tain registration accuracy and user perspective consistency. Visual elements such as edge highlights, opacity gradients, and interactive cursors are composited onto the physical anatomy and instrument surfaces in a manner that preserves depth cues and anatomical realism.

The use of the updated pose estimate for rendering ensures that the operative guidance overlay is perceptually stable, surgically accurate, and visually reliable throughout the procedure, enabling the user to perform navigation and decision-making tasks with continuous spatial confidence for both patient anatomy and operative instruments.

FIG. 10 is a flowchart 900 that illustrates an exemplary method for generating the guidance overlay data associated with the anatomical structure of the patient based on the visual parameter data, in accordance with an embodiment of the disclosure. FIG. 10 is explained in conjunction with elements from FIGS. 1, 2, 3, 4, 5, 6, 7, 8, and 9. With reference to FIG. 10, there is shown the flowchart 900. The operations of the exemplary method may be executed by any computing system, for example, by the system 500, the computing device 502, or the processor 502A of FIG. 6. The operations of the flowchart 900 may start at 902.

In an embodiment, the virtual anatomical model of the anatomical structure of the patient includes a one or more sets of layers, each of the one or more sets of layers corresponds to an anatomical layer associated with a region of the anatomical structure. In an embodiment, the virtual anatomical model is composed of one or more sets of layers, each digitally representing a distinct structural region of the patient's body. These may include skin, connective tissue, muscular regions, vascular structures, bone, pulmonary features, and pathological abnormalities such as effusions or fracture sites. Each of the one or more sets of layers corresponds to a well-defined anatomical zone or tissue plane and may be selectively rendered, occluded, highlighted, or modified based on contextual or procedural requirements. The layers are organized hierarchically or in parallel planes, depending on spatial configuration and clinical objectives.

At 902, the visual parameter data associated with each of the one or more sets of layers is received. In an embodiment, the computing device 502 or the processor 502A is configured to receive visual parameter data associated with each of the one or more sets of layers. The visual parameter data is associated with at least one of: transparency, color, transfer function, gradient, ambient occlusion, metallic, or sharpness. This visual parameter data defines how each layer is to be visually rendered during the augmented reality experience and is associated with at least one of: Transparency (e.g., percentage of opacity for anatomical layers), Color (e.g., fixed RGB value or dynamic based on procedural flags), Gradient (e.g., depth shading or scalar field visualization for procedural mapping), Sharpness (e.g., rendering resolution or anti-aliasing for edge clarity) The visual parameter data may be provided by a user interface, a configuration profile, a predefined procedural protocol, or calculated dynamically based on tracking confidence, user attention, or interaction state.

In an example, during thoracic surgery planning, the rib layer is configured to display with medium opacity and a steel-blue color gradient to allow visibility of underlying lung structures while preserving structural context. Simultaneously, the lung parenchyma layer may be displayed in semi-transparent red with high edge sharpness to delineate surgical margins around a suspected hemothorax.

In another example, the skin and soft tissue layers are rendered with low sharpness and high transparency during the incision planning phase but automatically revert to higher opacity and reduced gradient during alignment confirmation to enhance surface feature registration. The computing device 502 uses the visual parameter data to dynamically adjust each rendered layer within the operative guidance overlay, ensuring that the visualization remains contextually relevant and perceptually optimized for the user's viewpoint and task.

At 904, the guidance overlay data associated with the anatomical structure of the patient is generated based on the visual parameter data. In an embodiment, the computing device 502 or the processor 502A is configured to generate the guidance overlay data associated with the anatomical structure of the patient based on the visual parameter data.

The guidance overlay data includes a composite set of three-dimensional virtual constructs that are registered to the physical anatomy of the patient and intended for display through the wearable augmented reality interface device 506. These constructs may include anatomical landmarks, incision paths, fracture annotations, implant trajectories, organ boundaries, and other clinically relevant guidance elements that support surgical planning, navigation, or intervention.

The visual parameter data associated with each anatomical layer, such as, but not limited to, transparency, color, gradient, and sharpness is used to define the visual appearance and rendering properties of those elements when integrated into the final guidance overlay. The computing device 502 modifies each layer's appearance in accordance with this data, ensuring that the rendered guidance information is perceptually optimized for clinical clarity and spatial precision.

In one embodiment, the processor 502A applies a parameter set in which the ribcage layer is rendered at opacity, e.g., 40% in a blue gradient with high edge sharpness to allow simultaneous visualization of underlying soft tissues and precise rib contours. The lung parenchyma layer may be rendered in color, e.g., red with reduced gradient and transparency to emphasize the area of interest for procedural targeting. A fracture site marker may be overlaid with enhanced contrast and localized brightness based on visual parameter data associated with the pathology layer.

In another embodiment, the visual parameter data defines a gradient mapping across an entire anatomical structure, for example, a heatmap overlay indicating implant pressure or force distribution allowing the guidance overlay to communicate procedural feedback or planning constraints.

The guidance overlay data generated in this manner reflects not only the anatomical accuracy of the virtual model but also the context-sensitive visual design required for real-time augmented reality integration. The use of individualized visual parameter settings for each anatomical structure enables adaptive rendering strategies that improve the surgeon's ability to interpret complex layered anatomy during intraoperative decision-making.

FIG. 11 is a flowchart 1000 that illustrates an exemplary method for updating the virtual anatomical model of the anatomical structure of the patient based on the action data and the image data, in accordance with an embodiment of the disclosure. FIG. 11 is explained in conjunction with elements from FIGS. 1, 2, 3, 4, 5, 6, 7, 8, 9, and 10. With reference to FIG. 11, there is shown the flowchart 1000. The operations of the exemplary method may be executed by any computing system, for example, by the system 500, the computing device 502, or the processor 502A of FIG. 6. The operations of the flowchart 1000 may start at 1002.

At 1002, action data associated with an action is determined. In an embodiment, the computing device 502 is configured to determine action data associated with an action. The action is performed by the user on the anatomical structure of the patient. The action data is determined based on the sensor data. The action may include physical, gestural, or interaction-based events that occur during the surgical procedure and are relevant to clinical decision-making, spatial annotation, or procedural tracking. The action data is determined based on one or more measurements from the sensor data acquired through the set of sensors associated with the system 500. The sensor data may include information such as hand gestures, tool tip positions, gaze fixations, or orientation and motion characteristics of the wearable augmented reality interface device. The computing device 502 processes these inputs to identify discrete actions such as confirming an implant position, initiating an incision, interacting with a specific anatomical layer, or registering a landmark on the virtual anatomical model.

In one embodiment, the action is detected based on a gesture captured using AR hand controllers or vision-based tracking. For example, a tap or pointing motion made by the user toward a specific region of the patient's anatomy is interpreted as a selection or confirmation action. The action data determined in this case includes the anatomical location, timestamp, gesture type, and corresponding anatomical structure selected.

In another embodiment, the user performs an action by placing a tracked surgical instrument on a known anatomical point (e.g., the tip of a fractured rib), and the pose of the instrument is captured through the sensor array. The computing device 502 determines action data by correlating the instrument pose with the virtual anatomical model, thereby establishing a landmark confirmation or region tagging event.

In an additional embodiment, eye movement data received from eye-tracking sensors is used to infer an action. A prolonged fixation on a virtual implant or overlay label may be interpreted as an intent to activate, inspect, or adjust that element, and corresponding action data is generated to trigger the appropriate system behavior.

At 1004, the orientation data or the pose data of at least one of the virtual anatomical model, or the one or more virtual instrument models is updated to align the virtual anatomical model with the anatomical structure of the patient and the one or more virtual instrument models with the corresponding one or more operative instruments, based on the action data and the image data. In an embodiment, the computing device 502 is configured to perform this update so that procedural changes, clinical decisions, or real-time anatomical and instrument inputs captured during intraoperative interaction are reflected within the augmented reality environment.

The action data includes event-specific metadata indicating the type, location, and clinical intent of a user action, such as, but not limited to, landmark confirmation, tool interaction, or layer or instrument manipulation. The image data includes the preoperative or intraoperative medical imaging data used to construct the initial virtual anatomical model and virtual instrument models, such as computed tomography (CT) scans, magnetic resonance imaging (MRI) volumes, or CAD files of surgical tools.

The computing device 502 integrates the action data with the corresponding anatomical or instrument region defined in the image data to perform context-aware modifications of the orientation or pose of the models. These updates may include changes in anatomical layer visibility, adjustment of overlay boundaries, annotation of confirmed fracture sites, reconfiguration of implant guides, or realignment of virtual instrument models to their physical counterparts.

In one example, the user places a tracked pointer on a fractured rib segment, and the computing device 502 records the tip location as action data. The computing device 502 uses this input to update the pose of the virtual anatomical model by marking the corresponding rib structure as "fractured," changing its visual status, and enabling implant alignment overlays for that region, while also aligning any associated virtual instrument models with their physical positions.

In another embodiment, the user performs a gesture to remove a virtual soft tissue layer or to reposition a surgical tool representation from the current field of view. The action data is combined with the anatomical or instrument reference from the image data, prompting the computing device 502 to update the orientation or pose of the virtual model by hiding or adjusting transparency settings for the soft tissue layer and/or shifting the virtual instrument model to maintain correct alignment.

In an example, action data confirming implant placement is received, and the computing device 502 updates both the virtual anatomical model and the virtual instrument models to reflect the new implant geometry and tool position overlaid on the original bone segment. This update includes modifying the models' spatial structure, visual parameters, and procedural state flags to maintain accurate alignment between the augmented reality content and the physical surgical field.

FIG. 12 is a flowchart 1100 that illustrates an exemplary method for rendering an operative guidance overlay in association with the patient within a field of view of the user based on the guidance overlay data, in accordance with an embodiment of the disclosure. FIG. 12 is explained in conjunction with elements from FIGS. 1, 2, 3, 4, 5, 6, 7, 8, 9, 10, and 11. With reference to FIG. 12, there is shown the flowchart 1100. The operations of the exemplary method may be executed by any computing system, for example, by the system 500, the computing device 502, or the processor 502A of FIG. 6. The operations of the flowchart 1100 may start at 1102.

At 1102, the image data associated with the patient is received. In an embodiment, the system 500 is configured to receive image data associated with the patient. The image data indicates an anatomical structure of the patient. In another embodiment, the computing device 502 or the processor 502A may be configured to receive image data associated with the patient. The image data indicates an anatomical structure of the patient and a structure of each of the one or more operative instruments.

At 1104, one or more virtual models based on the image data is generated. In an embodiment, the system 500 is configured to generate one or more virtual models based on the image data. The one or more virtual models include at least one of: a virtual anatomical model of the anatomical structure of the patient, or one or more virtual instrument models associated with the one or more operative instruments. In another embodiment, the computing device 502 or the processor 502A may be configured to generate one or more virtual models based on the image data.

At 1106, the sensor data associated with at least one of: the user, the one or more operative instruments, or the patient is received. In an embodiment, the system 500 is configured to receive the sensor data associated with at least one of: the user, the one or more operative instruments, or the patient. In another embodiment, the computing device 502 or the processor 502A may be configured to receive the sensor data associated with at least one of: the user, the one or more operative instruments, or the patient.

At 1108, the guidance overlay data associated with the at least one of anatomical structure of the patient, or the one or more operative instruments is dynamically generated based on the virtual anatomical model and the sensor data. In an embodiment, the system 500 is configured to dynamically generate guidance overlay data associated with at least one of: the anatomical structure of the patient, or the one or more operative instruments, based on the one or more virtual models, and the sensor data. The guidance overlay data indicates the operative guidance overlay comprising one or more guidance markers associated with the patient, the one or more operative instruments, or both. In another embodiment, the computing device 502 or the processor 502A may be configured to dynamically generate guidance overlay data associated with at least one of: the anatomical structure of the patient, or the one or more operative instruments, based on the one or more virtual models, and the sensor data.

At 1110, the operative guidance overlay is rendered in association with the patient based on the guidance overlay data. In an embodiment, the system 500 is configured to render, using the wearable augmented reality interface device, the operative guidance overlay in association with the patient based on the guidance overlay data. The rendering includes continuous alignment of the virtual anatomical model with the patient and the continuous alignment of the one or more virtual instrument models with corresponding operative instrument of the one or more operative instruments. In another embodiment, the computing device 502 or the processor 502A may be configured to render, using the wearable augmented reality interface device, the operative guidance overlay in association with the patient based on the guidance overlay data.

Note that throughout the following discussion, numerous references may be made regarding servers, services, engines, modules, interfaces, portals, platforms, or other systems formed from or using computing devices. It should be appreciated that the use of such terms is deemed to represent one or more computing devices having at least one processor, such as the processors 502A, configured to or programmed to execute software instructions stored on a computer readable tangible, non-transitory medium, or also referred to as a processor-readable medium. For example, a server can include one or more computers operating as a web server, database server, or other type of computer server in a manner to fulfill described roles, responsibilities, or functions. Within the context of this document, the disclosed devices or systems are also deemed to include computing devices having a processor and a non-transitory memory storing instructions executable by the processor that cause the device to control, manage, or otherwise manipulate the features of the devices or systems.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "receiving" or "providing" or "determining" or "identifying" "or visualizing" or "comparing" or "storing" or "selecting" or "generating" or "changing" or "modifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiments also relate to an apparatus for performing the operations discussed herein. This apparatus may be specially constructed for the required purposes, or it may include a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

What is claimed is:

1. A system comprising:
   a wearable augmented reality interface device configured to present an operative guidance overlay within a field of view of a user;
   a set of sensors arranged in association with the wearable augmented reality interface device, wherein the set of sensors is configured to measure sensor data associated with at least one of: the user, one or more operative instruments, or a patient, and transmit the measured sensor data to one or more processors; and
   a computing device comprising a memory configured to store computer-executable instructions and the one or more processors configured to execute the computer-executable instructions to:
   receive image data associated with the patient, wherein the image data indicates an anatomical structure of the patient and a structure of each of the one or more operative instruments;
   generate one or more virtual models based on the image data, wherein the one or more virtual models comprise at least one of: a virtual anatomical model of the anatomical structure of the patient, or one or more virtual instrument models associated with the one or more operative instruments;
   receive the sensor data associated with at least one of: the user, the one or more operative instruments, or the patient;
   dynamically generate guidance overlay data associated with at least one of: the anatomical structure of the patient, or the one or more operative instruments, based on the one or more virtual models, and the sensor data, wherein the guidance overlay data indicates the operative guidance overlay comprising one or more guidance markers associated with the patient, the one or more operative instruments, or both; and
   render, using the wearable augmented reality interface device, the operative guidance overlay in association with the patient based on the guidance overlay data, wherein the rendering comprises continuous alignment of the virtual anatomical model with the patient and the continuous alignment of the one or more virtual instrument models with corresponding operative instrument of the one or more operative instruments.

2. The system of claim 1, wherein the one or more processors are further configured to:

identify and localize one or more spatial reference markers associated with the patient, the one or more operative instruments, or both, wherein the spatial reference markers comprise at least one of: a passive visual marker, a light-emitting optical marker, an electromagnetic marker, or any combination thereof;

spatially align at least one of: the virtual anatomical model with the anatomical structure of the patient, or the one or more virtual instrument models with the corresponding one or more operative instruments, based on sensor data;

periodically receive updated sensor data from the set of sensors; and continuously maintain the spatial alignment of at least one of: the virtual anatomical model with the anatomical structure of the patient, or the one or more virtual instrument models with the corresponding one or more operative instruments, as the patient or the operative instruments move relative to a user's viewpoint, based on the updated sensor data.

3. The system of claim 2, wherein the sensor data comprises at least one of: environment data, user interaction data associated with the user, orientation data associated with the user, pose data associated with the patient or the one or more operative instruments, or alignment data associated with the one or more spatial reference markers.

4. The system of claim 3, wherein the user interaction data associated with the user comprises at least one of: a gesture, a voice command, an eye movement, or a manual input provided via user-operated controls.

5. The system of claim 3, wherein the one or more processors are further configured to:

apply an algorithm to at least one of: the orientation data, or the pose data;

determine, based on application of the algorithm, latency-adjusted orientation data associated with the user and latency-adjusted pose data associated with the at least one of: the patient, or the one or more operative instruments; and generate the guidance overlay data associated with the anatomical structure of the patient, the one or more operative instruments, or both, based on the latency-adjusted orientation data and the latency-adjusted pose data.

6. The system of claim 5, wherein the one or more processors are further configured to:

generate an initial pose estimate of the operative guidance overlay based on the sensor data;

predict a pose at each new time step using a previous estimate and a dynamic model;

obtain a new measurement from the sensor data at each new time step;

update the initial pose estimate to determine an updated pose estimate by optimally blending the predicted pose and the new measurement, accounting for their respective uncertainties; and render the within the field of view of the user based on the updated pose estimate, such that the field of view appears spatially stable with respect to the anatomical structure of the patient, or the one or more operative instruments, or both.

7. The system of claim 5, wherein the one or more processors are further configured to:

determine action data associated with an action, wherein the action is performed by the user on the anatomical structure of the patient, and wherein the action data is determined based on the sensor data; and update the orientation data or the pose data of at least one of: the virtual anatomical model, or the one or more virtual instrument models to align the virtual anatomical model with the anatomical structure of the patient and the one or more virtual instrument models with the corresponding one or more operative instruments, based on the action data and the image data.

8. The system of claim 1, wherein the virtual anatomical model of the anatomical structure of the patient comprises one or more sets of layers, each of the one or more sets of layers correspond to an anatomical layer associated with a region of the anatomical structure, and wherein the one or more processors are further configured to:

receive visual parameter data associated with each of the one or more sets of layers, wherein the visual parameter data is associated with at least one of: transparency, color, transfer function, gradient, ambient occlusion, or sharpness; and generate the guidance overlay data associated with the anatomical structure of the patient based on the visual parameter data.

9. A method comprising:

receiving image data associated with a patient, wherein the image data indicates an anatomical structure of the patient and a structure of each of one or more operative instruments;

generating one or more virtual models based on the image data, wherein the one or more virtual models comprise at least one of: a virtual anatomical model of the anatomical structure of the patient, or one or more virtual instrument models associated with the one or more operative instruments;

receiving, from a set of sensors, sensor data associated with at least one of: a user, the one or more operative instruments, or the patient;

dynamically generating guidance overlay data associated with at least one of: the anatomical structure of the patient, or the one or more operative instruments, based on the one or more virtual models and the sensor data, wherein the guidance overlay data indicates an operative guidance overlay comprising one or more guidance markers associated with the patient, the one or more operative instruments, or both; and rendering, using a wearable augmented reality interface device, the operative guidance overlay in association with the patient based on the guidance overlay data, wherein the rendering comprises continuous alignment of the virtual anatomical model with the patient and the continuous alignment of the one or more virtual instrument models with a corresponding operative instrument of the one or more operative instruments.

10. The method of claim 9, further comprising:

identifying and localizing one or more spatial reference markers associated with the patient, the one or more operative instruments, or both, wherein the spatial reference markers comprise at least one of: a passive visual marker, a light-emitting optical marker, an electromagnetic marker, or any combination thereof;

spatially aligning at least one of: the virtual anatomical model with the anatomical structure of the patient, or the one or more virtual instrument models with the corresponding one or more operative instruments, based on sensor data;

periodically receiving updated sensor data from the set of sensors; and

continuously maintaining the spatial alignment of at least one of: the virtual anatomical model with the anatomical structure of the patient, or the one or more virtual instrument models with the corresponding one or more operative instruments, as the patient or the operative instruments move relative to a user's viewpoint, based on the updated sensor data.

11. The method of claim 10, further comprising:

applying an algorithm to at least one of: orientation data, or pose data;

determining, based on application of the algorithm, latency-adjusted orientation data associated with the user and latency-adjusted pose data associated with at least one of: the patient, or the one or more operative instruments; and generating the guidance overlay data associated with the anatomical structure of the patient, the one or more operative instruments, or both, based on the latency-adjusted orientation data and the latency-adjusted pose data.

12. The method of claim 11, further comprising:

generating an initial pose estimate of the operative guidance overlay based on the sensor data;

predicting a pose at each new time step using a previous estimate and a dynamic model;

obtaining a new measurement from the sensor data at each new time step;

updating the initial pose estimate to determine an updated pose estimate by optimally blending the predicted pose and the new measurement, accounting for their respective uncertainties; and rendering the operative guidance overlay within a field of view of the user based on the updated pose estimate, such that the operative guidance overlay appears spatially stable with respect to the anatomical structure of the patient, or the one or more operative instruments, or both.

13. The method of claim 11, further comprising:

determining action data associated with an action, wherein the action is performed by the user on the anatomical structure of the patient, and wherein the action data is determined based on the sensor data; and updating the orientation data or the pose data of at least one of: the virtual anatomical model, or the one or more virtual instrument models to align the virtual anatomical model with the anatomical structure of the patient and the one or more virtual instrument models with the corresponding one or more operative instruments, based on the action data and the image data.

14. The method of claim 9, wherein the virtual anatomical model of the anatomical structure of the patient comprises one or more sets of layers, each of the one or more sets of layers correspond to an anatomical layer associated with a region of the anatomical structure, and wherein the method further comprises:

receiving visual parameter data associated with each of the one or more sets of layers, wherein the visual parameter data is associated with at least one of: transparency, color, transfer function, gradient, ambient occlusion, metallic, or sharpness; and generating the guidance overlay data associated with the anatomical structure of the patient based on the visual parameter data.

15. A computer programmable product comprising a non-transitory computer-readable medium having stored thereon computer-executable instructions, which when executed by one or more processors, cause the one or more processors to carry out operations comprising:

receiving image data associated with a patient, wherein the image data indicates an anatomical structure of the patient and a structure of each of one or more operative instruments;

generating one or more virtual models based on the image data, wherein the one or more virtual models comprise at least one of: a virtual anatomical model of the anatomical structure of the patient, or one or more virtual instrument models associated with the one or more operative instruments;

receive, from a set of sensors, sensor data associated with at least one of: a user, the one or more operative instruments, or the patient;

dynamically generating guidance overlay data associated with at least one of: the anatomical structure of the patient, or the one or more operative instruments, based on the one or more virtual models and the sensor data, wherein the guidance overlay data indicates an operative guidance overlay comprising one or more guidance markers associated with the patient, the one or more operative instruments, or both; and rendering, using a wearable augmented reality interface device, the operative guidance overlay in association with the patient based on the guidance overlay data, wherein the rendering comprises continuous alignment of the virtual anatomical model with the patient and the continuous alignment of the one or more virtual instrument models with a corresponding operative instrument of the one or more operative instruments.

16. The computer programmable product of claim 15, wherein the operations further comprise:

identifying and localizing one or more spatial reference markers associated with the patient, the one or more operative instruments, or both, wherein the spatial reference markers comprise at least one of: a passive visual marker, a light-emitting optical marker, an electromagnetic marker, or any combination thereof;

spatially aligning at least one of: the virtual anatomical model with the anatomical structure of the patient, or the one or more virtual instrument models with the corresponding one or more operative instruments, based on sensor;

periodically receiving updated sensor data from the set of sensors; and continuously maintaining the spatial alignment of at least one of: the virtual anatomical model with the anatomical structure of the patient, or the one or more virtual instrument models with the corresponding one or more operative instruments, as the patient or the operative instruments move relative to a user's viewpoint, based on the updated sensor data.

17. The computer programmable product of claim 16, wherein the operations further comprise:

applying an algorithm to at least one of: orientation data, or pose data;

determining, based on application of the algorithm, latency-adjusted orientation data associated with the user and latency-adjusted pose data associated with the at least one of: the patient, or the one or more operative instruments; and generating the guidance overlay data associated with the anatomical structure of the patient, the one or more operative instruments, or both, based on the latency-adjusted orientation data and the latency-adjusted pose data.

18. The computer programmable product of claim 17, wherein the operations further comprise:

generating an initial pose estimate of the operative guidance overlay based on the sensor data;

predicting a pose at each new time step using a previous estimate and a dynamic model;

obtaining a new measurement from the sensor data at each new time step;

updating the initial pose estimate to determine an updated pose estimate by optimally blending the predicted pose and the new measurement, accounting for their respective uncertainties; and rendering the operative guidance overlay within a field of view of the user based on the updated pose estimate, such that the operative guidance overlay appears spatially stable with respect to the anatomical structure of the patient, or the one or more operative instruments, or both.

19. The computer programmable product of claim 16, wherein the operations further comprise:

determining action data associated with an action, wherein the action is performed by the user on the anatomical structure of the patient, and wherein the action data is determined based on the sensor data; and updating orientation data or pose data of at least one of: the virtual anatomical model, or the one or more virtual instrument models to align the virtual anatomical model with the anatomical structure of the patient and the one or more virtual instrument models with the corresponding one or more operative instruments, based on the action data and the image data.

20. The computer programmable product of claim 15, wherein the virtual anatomical model of the anatomical structure of the patient comprises one or more sets of layers, each of the one or more sets of layers correspond to an anatomical layer associated with a region of the anatomical structure, and wherein the operations further comprise:

receiving visual parameter data associated with each of the one or more sets of layers, wherein the visual parameter data is associated with at least one of: transparency, color, transfer function, gradient, ambient occlusion, metallic, or sharpness; and generating the guidance overlay data associated with the anatomical structure of the patient based on the visual parameter data.

* * * * *